US007285288B1

(12) United States Patent
Tormo et al.

(10) Patent No.: US 7,285,288 B1
(45) Date of Patent: *Oct. 23, 2007

(54) INHIBITION OF BCL-2 PROTEIN EXPRESSION BY LIPOSOMAL ANTISENSE OLIGODEOXYNUCLEOTIDES

(75) Inventors: Mar Tormo, Valencia (ES); Ana M Tari, Houston, TX (US); Gabriel Lopez-Berestein, Bellaire, TX (US); Timothy J McDonnell, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/381,747

(22) PCT Filed: Oct. 3, 1997
(Under 37 CFR 1.47)

(86) PCT No.: PCT/US97/18348

§ 371 (c)(1),
(2), (4) Date: Sep. 22, 1999

(87) PCT Pub. No.: WO98/14172

PCT Pub. Date: Apr. 9, 1998

(51) Int. Cl.
*C12Q 1/68* (2006.01)
*C07H 21/02* (2006.01)
*C07H 21/04* (2006.01)
*A01K 9/127* (2006.01)

(52) U.S. Cl. .................... 424/450; 435/91.1; 536/23.1; 536/24.3; 536/24.5; 514/44

(58) Field of Classification Search .................. 514/44; 435/6, 91.1, 91.3, 375, 325; 536/25.1, 23.2, 536/24.5, 24.3, 24.31, 24.33
See application file for complete search history.

(56) References Cited

U.S. PATENT DOCUMENTS

| 4,229,360 A | 10/1980 | Schneider et al. ........... 260/403 |
|---|---|---|
| 4,394,448 A | 7/1983 | Szoka, Jr. et al. ........... 435/172 |
| 4,469,863 A | 9/1984 | Ts'o et al. ..................... 536/27 |
| 4,480,041 A | 10/1984 | Myles et al. ................. 436/508 |
| 4,721,612 A | 1/1988 | Janoff et al. ................ 424/1.21 |
| 4,835,263 A | 5/1989 | Nguyen et al. ................ 536/27 |
| 4,837,028 A | 6/1989 | Allen ........................... 424/450 |
| 4,904,582 A | 2/1990 | Tullis ............................. 435/6 |
| 4,920,016 A | 4/1990 | Allen et al. .................. 424/450 |
| 4,924,624 A | 5/1990 | Suhadolnik et al. ........... 514/44 |
| 4,950,432 A | 8/1990 | Mehta et al. ................. 264/4.6 |
| 5,015,568 A | 5/1991 | Tsujimoto et al. .............. 435/5 |
| 5,030,442 A | 7/1991 | Uster et al. .................... 424/45 |
| 5,049,388 A | 9/1991 | Knight et al. ................ 424/450 |
| 5,087,617 A | 2/1992 | Smith ........................... 514/44 |
| 5,094,785 A | 3/1992 | Law et al. .................... 264/4.3 |
| 5,098,890 A | 3/1992 | Gewirtz et al. ................ 514/44 |
| 5,100,662 A | 3/1992 | Bolcsak et al. ............. 424/450 |
| 5,112,962 A | 5/1992 | Letsinger et al. ........... 536/25.3 |
| 5,135,917 A | 8/1992 | Burch .......................... 514/44 |
| 5,178,875 A | 1/1993 | Lenk et al. .................. 424/450 |
| 5,188,897 A | 2/1993 | Suhadolnik et al. ..... 428/402.2 |
| 5,202,429 A | 4/1993 | Tsujimoto et al. ......... 536/23.5 |
| 5,227,170 A | 7/1993 | Sullivan ..................... 424/450 |
| 5,248,671 A | 9/1993 | Smith .......................... 514/44 |
| 5,264,618 A | 11/1993 | Felgner et al. .............. 560/224 |
| 5,271,941 A | 12/1993 | Cho-Chung ................. 424/450 |
| 5,279,833 A | 1/1994 | Rose .......................... 424/450 |
| 5,279,957 A | 1/1994 | Gross ......................... 435/348 |
| 5,320,962 A | 6/1994 | Stiles et al. .............. 435/252.3 |
| 5,324,654 A | 6/1994 | Bredesen ..................... 435/376 |
| 5,376,646 A | 12/1994 | Pittrof et al. ................. 514/78 |
| 5,378,825 A | 1/1995 | Cook et al. .............. 536/25.34 |
| 5,417,978 A * | 5/1995 | Tari et al. .................... 424/450 |
| 5,459,251 A | 10/1995 | Tsujimoto et al. ......... 536/23.5 |
| 5,527,538 A | 6/1996 | Baldeschwieler ......... 424/1.21 |
| 5,539,085 A | 7/1996 | Bischoff et al. ............ 530/350 |
| 5,539,094 A | 7/1996 | Reed et al. ................ 536/23.5 |
| 5,560,923 A | 10/1996 | Rahman et al. ............. 424/450 |
| 5,565,337 A | 10/1996 | Diamond et al. .......... 435/70.2 |
| 5,583,034 A * | 12/1996 | Green et al. .................... 435/6 |
| 5,622,852 A | 4/1997 | Korsmeyer ................. 435/325 |
| 5,641,662 A | 6/1997 | Debs et al. ............... 435/172.1 |
| 5,661,018 A | 8/1997 | Ashley et al. ............ 435/172.3 |
| 5,665,710 A | 9/1997 | Rahman et al. ............... 514/44 |
| 5,696,248 A | 12/1997 | Peyman et al. ............. 536/22.1 |
| 5,705,385 A | 1/1998 | Bally et al. ............... 435/320.1 |
| 5,734,033 A | 3/1998 | Reed .......................... 536/23.1 |
| 5,750,669 A | 5/1998 | Rosch et al. ............... 536/24.3 |
| 5,756,122 A | 5/1998 | Thierry et al. ............. 424/450 |
| 5,817,811 A | 10/1998 | Breipohl et al. ............ 544/264 |
| 5,831,048 A | 11/1998 | Schwighoffer et al. .... 536/23.1 |

(Continued)

FOREIGN PATENT DOCUMENTS

CA        2171589        1/1996

(Continued)

OTHER PUBLICATIONS

Agrawal, "Antisense oligonucleotides: towards clinical trials" TIBTech, vol. 14, p. 376-387, Oct. 1996.*

(Continued)

*Primary Examiner*—Sean McGarry
*Assistant Examiner*—Kimberly Chong
(74) *Attorney, Agent, or Firm*—Fulbright & Jaworski L.L.P.

(57) ABSTRACT

The present invention provides novel compositions and methods for use in the treatment of Bcl-2-associated diseases like cancer, specifically, in the treatment of follicular lymphoma (FL). The compositions contain antisense oligonucleotides that hybridize to Bcl-2 nucleic acids, the gene products of which are known to interact with the tumorigenic protein Bcl-2. Used alone, or in conjunction with other antisense oligonucleotides, these compositions inhibit the proliferation of FL cancer cells.

46 Claims, 13 Drawing Sheets

U.S. PATENT DOCUMENTS

| | | | |
|---|---|---|---|
| 5,831,066 A | 11/1998 | Reed | 536/24.5 |
| 5,837,838 A | 11/1998 | Reed et al. | 536/23.1 |
| 5,855,911 A * | 1/1999 | Lopez-Berestein et al. | 424/450 |
| 5,874,224 A | 2/1999 | Bandman et al. | 435/6 |
| 5,874,553 A | 2/1999 | Peyman et al. | 536/22.1 |
| 5,891,714 A | 4/1999 | Ashley et al. | 435/320.1 |
| 5,908,635 A | 6/1999 | Thierry | 424/450 |
| 5,976,567 A | 11/1999 | Wheeler et al. | 454/450 |
| 5,981,501 A | 11/1999 | Wheeler et al. | 514/44 |
| 5,989,912 A | 11/1999 | Arrow et al. | 435/375 |
| 6,015,886 A | 1/2000 | Dale et al. | 536/23.1 |
| 6,030,954 A | 2/2000 | Wu et al. | 514/44 |
| 6,034,235 A | 3/2000 | Sugiyama et al. | 536/24.5 |
| 6,040,181 A | 3/2000 | Reed | 435/377 |
| 6,042,846 A * | 3/2000 | Lopez-Berestein et al. | 424/450 |
| 6,096,720 A | 8/2000 | Love et al. | 514/44 |
| 6,110,490 A | 8/2000 | Thierry | 424/450 |
| 6,120,794 A | 9/2000 | Liu et al. | 424/450 |
| 6,120,798 A | 9/2000 | Allen et al. | 424/450 |
| 6,126,965 A | 10/2000 | Kasid et al. | 424/450 |
| 6,136,965 A | 10/2000 | Bruice et al. | 536/25.3 |
| 6,211,162 B1 | 4/2001 | Dale et al. | 514/44 |
| 6,211,349 B1 | 4/2001 | Dale et al. | 536/23.1 |
| 6,277,832 B1 | 8/2001 | Sugiyama et al. | 514/44 |
| 6,277,981 B1 | 8/2001 | Tu et al. | 536/25.3 |
| 6,291,668 B1 | 9/2001 | Ziegler et al. | 536/24.5 |
| 6,326,487 B1 | 12/2001 | Peyman et al. | 536/24.5 |

FOREIGN PATENT DOCUMENTS

| | | |
|---|---|---|
| DE | 4110085 | 3/1991 |
| EP | 0 252 685 | 1/1988 |
| WO | WO88/04924 | 7/1988 |
| WO | WO89/06977 | 8/1989 |
| WO | WO90/09180 | 8/1990 |
| WO | WO90/10488 | 9/1990 |
| WO | WO91/16901 | 11/1991 |
| WO | WO92/21330 | 12/1992 |
| WO | WO93/07883 | 4/1993 |
| WO | WO93/11245 | 6/1993 |
| WO | 93/202200 | * 10/1993 |
| WO | WO93/20200 | * 10/1993 |
| WO | WO93/20200 | 10/1993 |
| WO | WO93/24653 | 12/1993 |
| WO | WO94/04545 | 3/1994 |
| WO | WO94/05259 | 3/1994 |
| WO | WO95/03788 | 2/1995 |
| WO | 95/08350 | * 3/1995 |
| WO | WO95/08350 | 3/1995 |
| WO | WO95/08350 | * 3/1995 |
| WO | WO95/28497 | 10/1995 |
| WO | WO96/27663 | 9/1996 |
| WO | WO96/40062 | 12/1996 |
| WO | WO97/07784 | 3/1997 |
| WO | WO98/14172 | 4/1998 |
| WO | WO98/56905 | 12/1998 |
| WO | WO 00/40595 | 7/2000 |
| WO | WO 02/17852 | 3/2002 |

OTHER PUBLICATIONS

Branch,"A good antisense molecule is hard to find", TIBS 23, p. 45-50, Feb. 1998.*

Crooke, "Antisense research and application" Springer, New York, p. 1-50, Jul. 1998.*

Gura, Science, vol. 278, p. 1041-1042, Nov. 1997.*

Golden, Time, vol. 151, (19), p. 44.*

Crooke, ST, Basic Principles of Antisense Therapeutics. Antisense Research and Application (1998), Chapter 1, Springer-Verlag, New York.*

Crooke, St, Potential roles of antisense technology in cancer chemotherapy. Oncogene (2000), vol. 19, 6651-6659. Macmillan Publishers Ltd.*

Korsmeyer et al. Bcl-2?Bax: a rheostat that regulates an anti-oxidant pathway and cell death. Cancer Biology, 1993, vol. 4: 327-332. Academic Press Ltd.*

M.T. Almazan et al., "Methylphosphonate-containing oligonucleotides efficiently and specifically inhibit Bcl-2 and erbB-2 expression in vitro," *Proc. Amer. Assoc. Cancer Res.*, 37:353, Abstract No. 2407, Mar. 1996.

M. Tormo et al., "Antitumor activity of liposomal-bcl-2-antisense ologonucleotides in follicular lymphoma," *Proc. Amer. Assoc. Cancer Res.*, 37:173, Abstract No. 1190, Mar. 1996.

Fred D. Ledley, "Non-viral gene therapy," *Current Opinion in Biotechnology*, 5:626-636, 1994.

Yongyut Rojanasakul, "Antisense oligonucleotide therapeutics: drug delivery and targeting," *Adv. Drug Delivery Reviews*, 18:115-131, 1996.

Abubakr et al., Effectiveness of Bcl-2 antisense oliogodeoxynucleotides (AS-ODN) against human follicular small-cleaved cell lymphoma (FSCCL)-SCID mice xenograft model, *Blood*, 84 (10 Suppl. 1) 374A, 1994.

Agris et al., "Inhibition of vesicular stomatitis virus protein synthesis and infection by sequence-specific oligodeoyribonucleoside methylposphonates," *Biochemistry*, 25:6268-6275, 1986.

Akhtar et al., "Interactions of antisense DNA oligonucleotide analogs with phospholipid membranes (liposomes)," *Nucleic Acids Research*, 19(20): 5551-5559, 1991.

Akhtar et al., "Release of antisense oligdeoynucleotide analogues from liposomes: implications for cellular transport and drug delivery," 128th Meeting of British Pharmaceutical Conference 1991, United Kingdom, Sep. 10-13, 1991, *J. Pharm. Pharmacol.*, 43 (Suppl.):Abstrast 24P, 1991.

Aktar et al., "Lipsome Delivery of Antisense Methylphosphonate and Phosphorothioate Oligonucleotides: A Study with MLV, FATMLV, and LUV Liposomes," *Proceed. Intern. Symp. Control. Rel. Bioact. Mater.*, 19:345-346, 1992.

Allsopp et al., "The Proto-Oncogene bcl-2 Can Selectively Rescue Neurotrophic Factor-Dependent Neurons from Apoptosis," *Cell*, 73: 295, 1993.

Arad et al., "Use of reconstituted sendai virus envelopes for fusion-mediated microinjection of double-stranded RNA: Inihibition of protein synthesis in interfron-treated cells," *Biochimica et Biophysica Acta*, 859:88-94, 1986.

Bakhshi et al., "Cloning the Chromasomal Breakpoint of t(14;18) Human Lymphomas: Clustering around $J_H$ on Chromosome 14 and near a Transcriptional Unit on 18," *Cell*, 41:899, 1985.

Bennett et al., "Cationic lipids enhance cellular uptake and activity of phosphorothioate antisense oligonucleotides," *Molecular Pharmacology*, 41(6): 1023-1033, 1992.

Boise, et al., "bcl-x, a bcl-2-Related Gene That Functions as a Dominant Regulator of Apoptotic Cell Death", *Cell*, 74:597-608, 1993.

Boiziau et al., "Modified oligonucleotides in rabbit reticulocytes: uptake, stability and antisense properties," Biochimie, 73:1403-1408, 1991.

Borzillo et al., "*Bcl-2* Confers Growth and Survival Advantage to Interleukin 7-dependent Early Pre-B Cells Which Become Factor Independent by a Multistep Process in Culture," *Oncogene*, 7:869, 1992.

Bradbury et al., "Down-Regulation of bcl-2 in AML Blasts by All-Trans Retinoic Acid and Its Relationship of CD34 Antigen Expression," *British Journal of Haemaltology*, 94:671-675, 1996.

Budker et al., "Cell membranes as barriers for antisense constructions," *Antisense Research and Development*, 2:177-184, 1992.

Campos et al., "Effects of *BCL-2* Antisense Oligodeoxynucleotides on In Vitro Proliferation and Survival of Normal Marrow Progenitors and Leukemic Cells," *Blood*, 84:595, 1994.

Capaccioli et al., "Cationic lipids improve antisense oligonucleotide uptake and prevent degradation in cultured cells and in human serum," *Biochemical and Biophysical Research Communications*, 197(2):818-825, 1993.

Capaccioli et al., "A bcl-2/IgH Antisense Transcript Deregulates bcl-2 Gene Expression in Human Follicular Lymphoma t(14;18) Cell Lines," Oncogene, 13:105-115, 1996.

Cazals-Hatem et al., "Molecular Cloning and DNA Sequence Analysis of cDNA Encoding Chicken Homologue of the Bcl-2 Oncoprotein," *Biochim. Biophys. Acta*, 1132:109, 1992.

Chao, et al., "Bcl-$x_L$ and Bcl-2 Repress a Common Pathway of Cell Death," *J. Exp. Med.*, 182:821-828, 1995.

Chen et al., "Suppression of *Bcl-2* Messenger RNA Production May Mediate Apoptosis after Ionizing Radiation, Tumor Necrosis Factor α, and Ceramide," *Cancer Res.*, 55:991-994, 1995.

Cheng et l., "Bax-independent inhibition of apoptosis by Bcl-$x_L$," *Nature*, 279:554-556, 1996.

Chen-Levy and Cleary, "Membrane Topology of the Bcl-2 Protooncogenic Protein Demonstrated in Vitro," *J. Biol. Chem.* 265:4929, 1990.

Chen-Levy et al., "The *bcl-2* Candidate Proto-Oncogene Products Is a 24-Kilodalton Integral-Membrane Protein Highly Expressed in Lymphoid Cell Lines and Lymphomas Carrying the t(14;18) Translocation," *Mol. Cell. Biol.*, 9:701, 1989.

Chittenden et al., "Induction of apoptosis by the Bcl-2 homologue Bak," *Nature*, 374:733, 1995.

Choi et al., "The role of bcl-$X_L$ in CD40-mediated rescue from anti-μ-induced apoptosis in WEHI-231 B lymphoma cells," *Eur. J. Immunol.*, 25:1352-1357, 1995.

Citro et al., "Chemical modification of ligands for cell receptors to introduce foreign compounds into the cells," *Colon & Rectum*, 37(2):S127-S132, 1994.

Clarenc et al., "Delivery of Antisense Oligonucleotides by poly(L-Lysine) Conjugation and Liposome Encapsulation," *Anti-Cancer Drug Design*, 8:81-94, 1993.

Clarke et al., "A recombinant *bcl-$x_s$* adenovirus selectively induces apoptosis in cancer cells but not in normal bone marrow cells," *Proc. Natl. Acad. Sci. USA*, 92:11024-11028, 1995.

Cleary et al., "Cloning and Structural Analysis of cDNAs for *bcl-2* and a Hybrid *bcl-2*/Immunoglobulin Transcript Resulting from the t(14:18) Translation," *Cell*, 47:19, 1986.

Cotter et al., "Antisense oligoucleotides supress B-cell lymphoma growth in a SCID-hu mouse model," *Oncogene*, 9:304-3055, 1994.

Cuende et al., Programmed cell death by *bcl-2*-dependent and independent mechanisms in B lymphoma cells, *EMBO J.*, 12:1555-1560, 1993.

Datta et al., "Overexpression of Bcl-$x_L$ by Cytotoxic Drug Exposure Confers Resistance to Ionizing Radiation-induced Internucleosomal DNA Fragmentation," *Cell Growth & Differentiation*, 6:363-370, 1995.

Dole et al., "Bcl-$x_L$ Is Expressed in Neuroblastoma Cells and Modulates Chemotherapy-Induced Apoptosis," *Cancer Res.*, 55:2576-2582, 1995.

Duke et. al, "Morphological, biochemical and flow cytometric assays of apoptosis," *In:* Coligan et. al (eds) Current protocols in immunology, vol. 1., New York: John Wiley & sons, p. 3.17.1, 1991.

Eguchi et al., "Isolation and Characterization of the Chicken *bcl-2* Gene: Expression in a Variety of Tissues Including Lymphoid and Neuronal Organs in Adult and Embryo," *Nucl. Acids. Res.*, 20:4187, 1992.

Frankowski et al., "Function and expression of the *Bcl-x* gene in the developing and adult nervous system," *NeuroReport*, 6:1917-1921, 1995.

Garcia et al., "Prevention of Programmed Cell Death of Sympathetic Neurons by the *bcl-2* Prot-Oncogene," *Science*, 258:302, 1992.

Gerwirtz et al., "Facilitating oligonucleotide delivery: helping antisense delivery on its promise," *Proc. Natl. Acad. Sci. U.S.A.*, 93: 3161-3163, 1996.

Gomez-Manzano et al., "Bax, Bcl-2 and p53 Interactions Modulate p53-Induced Apoptosis in Glioma Cells," *Proceedings of the American Association for Cancer Research*, 37:204, Abstract 1397, Mar. 1996.

González-García et al., " *bcl-x* is expressed in embryonic and postnatal neural tissues and functions to prevent neuronal cell death," *Proc. Natl. Acad. Sci. USA.*, 92:4304-4308, 1995.

González-García et al., "*bcl-$x_L$* is the major *bcl-x* mRNA form expressed during murine development and its product localizes to mitochondria," *Development*, 120:3033-3042, 1994.

Gottschalk et al., "Identification of immunosuppressant-induced apoptosis in a murine B-cell line and its prevention by bcl-x but not bcl-2," *Proc. Natl. Acad. Sci. USA.*, 91:7350-7354, 1994.

Gottschalk et al., "The ability of Bcl-$x_L$ and Bcl-2 to prevent apoptosis can be differentially regulated," *Death and Differentiation*, 3:113-118, 1996.

Graninger et al., "Expression of bcl-2 and bcl-2-Ig fusion transcripts in normal and neoplastic cells," *J. Clin. Invest.*, 80:1512, 1987.

Grever and Chabner, "Cancer Drug Discovery and Developoment," *Cancer Principles & Practice of Oncology*, 5th Edition, Lippicott-Raven Publishers, 19:385-394, 1997.

Grillot et al., "*bcl-x* Exhibits Regulated Expression During B Cell Development and Activation and Modulates Lymphocyte Survival in Transgenic Mice," *J. Exp. Med.*, 183:381-391, 1996.

Hockenberry et al., "Bcl-2 is an inner mitochondrial membrane protein that blocks programmed cell death," *Nature*, 348:334, 1990.

Jäättelä et al., "Bcl-x and Bcl-2 inhibit TNF and Fas-induced apoptosis and activation of phospholipase $A_2$ in breast carcinoma cells," *Oncogene*, 10: 2297-2305, 1995.

Jasty et al., "*bcl-$x_L$*, A Gene Which Regulates Programmed Cell Death, Is Expressed In Neuroblastoma Tumor Cell Lines (abstract)," *Clinical Res.*, 42:416A, 1994.

Juliano et al., "Lipsomes as a Drug Delivery System for Antisense Oligodeoxynucleotides Encapsulated by Liposomes," *Antisense Research and Development*, 2:165-176, 1992.

Kaneda et al., "Increased Expression of DNA cointroduced with nuclear protein in adult rat liver," *Science*, 242:375-378, 1989.

Kato et al., "Expression of hepatitis B virus surface antigen in adult rat liver," *J. Biol. Chem.*, 266:3361-3364, 1991.

Keller et al., "Synthesis and hybridization properties of oligonucleotides containing 2'-O-modified ribonucleotides," *Nucleic Acids Research*, 21(19):4499-4505, 1993.

Kiefer et. al, "Modulation of apoptosis by the widely distributed Bcl-2 homologue Bak," *Nature*, 374: 736, 1995.

Kitada et al., "Investigations of antisense oligonucleotides targeted against bcl-2 RNAs," *Antisense Res. Dev.*, 3:157, 1993.

Kozopas et al., "*MCL-1*, a gene expressed in programmed myeloid cell differentiation, has sequence similarity to *BCL-2,*" *Proc. Nat'l Acad. Sci. USA*, 90:3516, 1993.

Krajewski et al., "Immunohistochemical Analysis of In Vivo Patterns of Bcl-x Expression," *Cancer Res.*, 54:5501-5507, 1994.

Kramer et al., "Self-specific T lymphocyte lines as vehicles for gene therapy: myelin specific T cells carrying exogenous nerve growth factor gene (abstract)," *J. Cell. Biochem.*, Suppl. o(17 Part E):215, 1993.

Krieg et al., "Modification of antisense phosphodiester oligodeoynucleotides by a 5' cholesteryl moiety increase cellular association and improves efficacy," *Proc. Natl. Acad. Sci., USA*, 90:1048-1052, 1993.

Leonetti et al., "Antibody-targeted liposomes containing oligodeoyribonucleotides complementary to viral RNA selectively inhibit viral replication," *Proc. Natl. Acad. Sci. USA*, 87:2448-2451, 1990.

Lin et. al, "Characterization of A1, a novel hemopoietic-specific early-response gene with sequence similarity to BCL-2," *J. Immunol.*, 151:1979, 1993.

Loke et al., "Characterization of oligonucleotide transport into living cells," *Proc. Natl. Acad. Sci. USA*, 86:3474-3478, 1989.

Loke et al., "Delivery of c-*myc* Antisense Phosphorothioate Oligodeoxynucleotides to Hematopoetic Cells in Culture by Lipsome Fusion: Specific Reduction in c-*myc* Protein Expression Correlates with Inhibition of Cell Growth and DNA Synthesis," *Current Topics in Microbiology and Immunology, Mechanisms in B-Cell Neoplasis*, 141:282-289, 1988.

Marin et al., "Complementation and Cell Death Regulation By Bcl-2, p53 and c-myc During In Vivo Lymphomagenesis," *Journal of Cellular Biochemistry*, Supplement 19B, p. 286, Abstract B8-224, Feb. 5-Mar. 15, 1995.

Martiat et al., "Retrovirally transduced antisense sequences stably suppress $P210^{BCR-ABL}$ epression and inhibit the proliferation of BCR/ABL-containing cell lines," *Blood*, 81(2):502-509, 1993.

Masserano et al., "Dopamine Induces Apoptotic Cell Death of a Catecholaminergic Cell Line Derived from the Central Nervous System," Molecular Pharmacology, 50:1309-1315, 1996.

McCarthy et al., "Apoptosis in the development of the immune system: Growth factors, clonal selection and *bcl-2*," Cancer Metastasis Reviews, 11:157-178, 1992.

McDonnell et al., "Cell Death Suppression by Bcl-2 Is Associated with Altered Nuclear-Cytoplasmic Trafficking," Proceedings of the American Association for Cancer Research, 37:16, Abstract 111, Mar. 1996, abstract only.

McDonnell et. al, "Bcl-2-immunoglobulin transgenic mice demonstrate extended B cell survival and follicular lymphoproliferation," Cell, 57:79, 1989.

McDonnell, et al., "The bcl-2-Immunoglobulin Transgenic Mouse: A Model of the t(14;18) Translocation in Human Follicular Lymphoma," Transgene, 1:47, 1993.

Miller et al., "Gene Transfer and antisense nucleic acid techniques," Parasitology Today, 10(3):92-97, 1994.

Miller, "Oligonucleoside methylphosphonates as antisense reagents," Bio/Technology, 9:358-362, Apr. 1991.

Minn et al., "Expression of Bcl-$x_L$ can Confer a Multidrug Resistance Phenotype," Blood, 86:1903-1910, 1995.

Miyashita et. al, "Tumor suppressor p53 is a regulator of bcl-2 and bax gene expression in vitro and in vivo," Oncogene, 9:1799, 1994.

Moody et al., "Regiospecific inhibition of DNA duplication by antisense phosphate-methylated oligodeoynucleotides," Nucleic Acids Research, 17(12):4769-4782, 1989. (Abstract).

Nicolau et al., "Liposomes as carriers for in vivo gene transfer and expression," Methods in Enzymology, 149:157-176, 1987.

Núñez et al., "BCL-X is expressed in embryonic and adult neuronal tissues and its expression prevents neuronal cell death (abstract)," J. Cell. Biochem., Supplement 0 (19B), B8-438, p. 317, 1995. abstract only.

Núñez et al., "Deregulated BCL-2 gene expression selectively prolongs survival of growth factors-deprived hemopoietic cell lines," J. Immunol., 144:3602, 1990.

Oltvai et al., "Bcl-2 Heterodimerizes In Vivo with a Conserved Homolog, Bax, That Accelerates Programmed Cell Death", Cell 74:609-619, 1993.

Oppenheim et al., "Brain-derived neurotrophic factor rescues developing avian motoneurons fron cell death," Nature, 360:755-757, 1992.

Pocock et al., "In vivo supresion of B-cell lymphoma Bcl-2 antisense oligonucleotides," Blood, 82 (Suppl. 1), 200A, 1993, abstract only.

Raff, M.C., "Social controls on cell survival and cell death," Nature, 356:397-400, 1992.

Reed et al., "Antisense-Mediated Inhibition Of BCL-2 Protooncogene Expression And Leukemic Cell Growth And Survival: Comparisons Of Phosphodiester and Phosphorothioate Oligodeoxynucleotides," Cancer Res., 50: 6565, 1990.

Reed et al., "Regulation of *bcl-2* Proto-Oncogene Expression During Normal Human Lymphocyte Proliferation," Science, 236:1295, 1987.

Reed et al., "Bcl-2-mediated tumorigenicity in a human T-lymphoid cell line: synergy with c-myc and inhibition by Bcl-2 antisense," Proc. Nat'l Acad. Sci. USA, 87:3660, 1990b.

Reed, et al., "Bcl-2: prevention of apoptosis as a mechanism of drug resistance," Hematol. Oncol. Clin. North Am., 9:451, 1995.

Renneisen et al., "Inhibition of epression of human immunodeficiency virus-l in vitro by antibody-targeted liposomes containing antisense RNA to the *env* region," The Journal of Biological Chemistry, 265(27):16337-16342, 1990.

Ropert et al., "Inhibition of the Friend Retrovirus by Antisense Oligonucleotides Encapsulated in Liposomes: Mechanism Action," Pharmaceutical Research, 10(10):1427-1433, Apr. 1993.

Sato et al., "Interactions among members of the Bcl-2 protein family analyzed with a yeast two-hybrid system," Proc. Natl. Acad. Sci. USA., 91:9238-9242, 1994.

Schendel et al., "Channel Formation by Antiapoptotic Protein Bcl-2," Proc. Natl. Acad. Sci. USA, 94:5113-5118, 1997.

Schott, et al., "Bcl-$x^L$ protects cancer cells from p53-mediated apoptosis," Oncogene, 11(7):1389-1394, 1995.

Schott et al., "BCL-$X_L$ Protects Cells from P53-Mediated Apoptosis", Journal of Investigative Medicine 43 (Suppl. 3) 458A, 1995, abstract.

Sedlak et al., "Multiple Bcl-2 family members demonstrate selective dimerization with Bax," Proc. Nat'l Acad. Sci. USA, 92:7834, 1995.

Sentman et al., "bcl-2 Inhibits Multiple Forms of Apoptosis but Not Negative Selection in Thymocytes," Cell, 67:879, 1991.

Shea et al., "Synthesis, hybridization properties and antiviral activity of lipid-oligodeoynucleotide conjugates," Nucleic Acids Research, 18(13):3777-3783, 1990.

Siegel et al., "Inhibition of thymocyte apoptosis and negative and antigenic selection in *bcl-2* transgenic mice," Proc. Natl. Acad. Sci. USA, 89:7003, 1992.

Skorski et al., "Gene-targeted Specific Inhibition of Chronic Myeloid Leukemia Cell Growth by BCR-ABL Antisense Oligodeoxynucleotides," Folia Histochemica et Cytobiologica, 29(3):85-90, 1991.

Stein et al., "Antisense oligonucleotides as thrapeutic agents—is the bullet really magical?," Science, 261:1004-1012, 1993.

Stein et al., "Oligodeoynucleotides as ihbitors of gene epression: A review," Cancer Research, 48(10):2635-2944, 1988.

Strasser et al., "bcl-2 Transgene Inhibits T Cell Death and Perturbs Thymic Self-Censorship," Cell, 67:889, 1991.

Strasser et al., "Enforced *BCL2* Expression in B-lymphoid Cells Prolongs Antibody Responses and Elicits Autoimmune Disease," Proc. Natl. Acad. Sci. USA, 88:8661, 1991.

Stull et al., "Antigene, ribozyme and aptamer nucleic acid drugs: progress and prospects, pharmaceutical research," 12(4):465-483, 1995.

Sumantran et al., "Overexpression of Bcl-$x_S$ Sensitizes MCF-7 Cells to Chemotherapy-Induced Apoptosis," Cancer Res., 55:2507-2510, 1995.

Szczylik et al., Selective inhibition of leukemia cell proliferation by BCR-ABL antisense oligodeoynucleotides,,Science, 253:562-565, 1991.

Taj et al., "Inhibition of $P210^{BCR/ABL}$ epression in K562 cells by electroporation with an Antisense oligonucleotide," Leukemia and Lymphoma, 3:201-208, 1990.

Tari et al., "Lipsomal Delivery of Methylposphonate Antisense Oligodeoxynucleotides in Chronic Myelogenous Leukemia," Blood, 84(2):601-607, Jul. 1994.

Thierry et al., "Liposomal delivery as a new approach to transport antisense oligonucleotides," Gene Regulation, Biology of Antisense RNA and DNA, 1: 147-161, 1992.

Thierry et al., Intracellular Availability of Unmodified, Phosphorothioated and Liposomally Encapsulated Oligodeoxynucleotides for Antisense Activity, Nucleic Acids Research, 20(21):5691-5698, Sep. 1992.

Thierry et al., "Modulation of multidrug Resistance by Antisense Oligodeoxynucleotides Encapsulated by Liposomes," Proceedings of the American Association for Cancer, Preclinical Pharmacology/Experimental Therapeutics, Abstract 2578, 32:443, Mar. 1991.

Thierry et al., Overcoming Multidrug Resistance in Human Tumor Cells Using Free and Liposomally Encapsulated Antisense Oligodeoxynucleotides,: Biochemical and Biophysical Research Communications, 190(3):952-960, Feb. 1994.

Thompson, C. B., "Apoptosis in the Pathogenesis and Treatment of Disease," Science, 267:1456-1462, 1995.

Tidd et al., "Evaluation of N-*ras* oncogene anti-sense, sense and nonsense sequence methylphosphonate oligonucleotide analogues," Anti-Cancer Drug Design, 3:117-127, 1988.

Tidd et al., "Partial protection of oncogene, anti-sense oligodeoynucleotides against serum nuclease degradation using terminal methylphosphonate groups," Be. J. Cancer, 60:343-350, 1989.

Tormo et al., "Antitumor Acivity of Liposomal-Bcl-2-Antisense Oligonucleotides in Follicular Lymphoma," Proceedings of the American Association for Cancer Research, 37:173, Abstract 1190, Mar. 1996.

Tsuchida et al., "Iron-ligand bonding properties of synthetic iron-porphyrin complees with oygen transporting ability in aqueous media," J. Chem. Soc. Dalton Transactions, 10:2455-2458, 1987.

Tsujimoto and Croce, "Analysis of the structure, transcripts, and protein products of bcl-2, the gene involved in human follicular lymphoma," *Proc. Natl. Acad. Sci. USA*, 83:5214, 1986.

Tsujimoto et. al, "Characterization of the protein product of bcl-2, the gene involved in human follicular lymphoma," *Oncogene*, 2:3, 1987.

Tsujimoto et. al, "The t(14;18) chromosome translocation involved in B-cell neoplasms result from mistakes in VDJ joining," *Science*, 229:1390, 1985.

Uhlmann et al., "Antisense oligonucleotides: a new therapeutic principal," *Chemical Reviews*, 90(4):543-584, 1990.

Vasanthakumar et al., "Modulation of drug resistance in a daunorubicin resistant subline with oligonucleoside methylphosphonates," *Cancer Communications*, 1(4):225-232, 1989.

Vaux et al., "*Bcl-2* gene promotes haemopoietic cell survival and cooperates with *c-myc* to immortalize pre-B cells," *Nature*, 335:440, 1988.

Wagner, "Gene inhibition using antisense oligodeoynucleotides," *Nature*, 372:333-335, 1994.

Webb et al., "Extrathymic Tolerance of Mature T Cells: Clonal Elimination as a Consequence of Immunity," *Cell*, 63:1249, 1990.

Weber-Nordt et al., "Interleukin-10 Increases Bcl-2 Expression and Survival in Primary Human CD34+ Hematopoietic Progenitor Cells," *Blood*, 88(7):2549-2558, 1996.

Weiss, "Upping the antisense ante scientists bet on profits from reverse genetics," *Science News*, 139:108-109, 1991.

Wickstrom, "Antisense DNA therapeutics neutral analogs and their stereochemistry," *Raven Press Ser. Mol. Cell. Biol.*, 1:119-132, 1992.

Williams, G.T., "Programmed Cell Death: Apoptosis and Oncogenesis," *Cell*, 65:1097-1098, 1991.

Wong et al., "Appearance of β-lactamase activity in animal cells upon liposome-mediated gene transfer," *Gene*, 10:87-94, 1980.

Wrone-Smith, et al., "Discordant Expression of Bcl-x and Bcl-2 by Keratinocytes in Vitro and Psoriatic Keratinocytes in Vivo," *Am. J. Pathology*, 146:1079-1088, 1995.

Wu-Pong, "Oligonucleotides: Opportunities for drug therapy and research, pharmaceutical technology," 18:102-114, 1984.

Yang et al., "Bad, a Heterodimeric Partner for Bcl-$X_L$ and Bcl-2, Displaces Bax and Promotes Cell Death," *Cell*, 80:285, 1995.

Yeoman et aL, "Lipofectin enhances cellular uptake of antisense DNA while inhibiting tumor cell growth", *Antisense Research and Development*, 2:51-59, 1992.

Yin et. al, "BH1 and BH2 domains of Bcl-2 are required for inhibition of apoptosis and heterodimerization with Bax," *Nature*, 369: 321, 1994.

Zhang et al., "Gene therapy for the peripheral nervous system rat neuritogenic T cell line carry mouse nerve growth factor gene (abstract)," *J. Cell. Biochem.*, Suppl. 0 (17 Part E):SZ-116, 1993.

Zhang et al., "BCL2 Regulates Neural Differentiation," Proc. Natl. Acad. Sci. USA, 93:4504-4508, 1996.

Zon, "Pharmaceutical considerations," *Oligodeoxynucleotides*, Jack S. Cohen, Ed., CRC Press, 11:233-247, 1989.

Agrawal et al., "Antisense therapeutics: is it as simple as complementary base recognition," Molecular Medicine Today, 6:72-81, 2000.

Aisenberg, "Coherent view of non-Hodgkin's lymphoma," *J. Clin. Oncol.*, 13(10):2656-2675, 1995.

Baichwal and Sugden, "Vectors for gene transfer derived from animal DNA viruses: Transient and stable expression of transferred genes," *In:* Kucherlapati R, (ed.) Gene transfer. New York: Plenum Press, pp. 117-148, 1986.

Bangham et al., "Diffusion of univalent ions across the lamellae of swollen phospholipids," *J. Mol. Biol.*, 13:238-252, 1965.

Benvenisty and Reshif, "Direction introduction of genes into rats and expression of the genes," *Proc. Nat'l Acad. Sci. USA*, 83:9551-9555, 1986.

Chang et al., "Foreign gene delivery and expression in hepatocytes using a hepatitis B virus vector," ABSTRACT, *Hepatology*, 14(4):124A, 1991.

Chen and Okayama, "High-efficiency transfection of mammalian cells by plasmid DNA," *Mol. Cell Biol.*, 7(8):2745-2752, 1987.

Chirila et al., "The use of synthetic polymers for delivery of therapeutic antisense oligodeoxynucleotides," *Biomaterials*, 23:321-342, 2002.

Coffin, "Retroviridae: the viruses and their replication," *In: Virology*, Fields et al. (eds.), New York: Raven Press, pp. 1767-1847, 1996.

Cotter et al., "Human Bcl-2 antisense therapy for lymphomas," *Biochimica et Biophysica Acta*, 1489:97-106, 1999.

Coupar et al., "A general method for the construction of recombinant vaccinia virus expressing multiple foreign genes," *Gene*, 68:1-10, 1988.

Crystal, *Science*, 270:404-410, 1995.

Deamer and Uster, "Liposome Preparation: Methods and Mechanisms," *LIPOSOMES*, M. Ostro ed. (1983).

Dubensky et al., "Direct transfection of viral and plasmid DNA into the liver or spleen of mice," *Proc. Nat'l Acad. Sci. USA*, 81:7529-7533, 1984.

Fecheimer et al., "Transfection of mammalian cells with plasmid DNA by scrape loading and sonication loading," *Proc. Nat'l Acad. Sci. USA*, 84(23):8463-8467, 1987.

Fraley et al., "Entrapment of a bacterial plasmid in phospholipid vesicles: potential for gene transfer," *Proc. Nat'l Acad. Sci. USA*, 76(7):3348-3352, 1979.

Friedman et al., "CCAAT/enhancer-binding protein activates the promoter of the serum albumin gene in cultured hepatoma cells," *Genes & Devel.* 3:1314-1322, 1989.

Ghosh and Bachhawat, "Targeting of liposomes to hepatocytes," *In:* Wu G. Wu C ed., Liver diseases, targeted diagnosis and therapy using specific receptors and ligands, New York: Marel Dekker, pp. 87-103, 1991.

Gleave et al., "Targeting bcl-2 gene to delay androgen-independent progression and enhance chemosensitivity in prostate cancer using antisense bcl-2 oligodeoxynucleotides," *Urology*, 54(Suppl 6A):36-46, 1999.

Gopal, "Gene transfer method for transient gene expression, stable transformation, and cotransformation of suspension cell cultures," *Mol. Cell Biol.*, 5:1188-1190, 1985.

Graham and van der Eb, "A new technique for the assay of infectivity of human adenovirus 5 DNA", *Virology*, 52:456-467, 1973.

Graham et al., "Characteristics of a human cell line transformed by DNA from human adenovirus type 5," *J. Gen. Virol.*, 36:59-72, 1977.

Harland and Weintraub, "Translation of mammalian mRNA injected into *Xenopus oocytes* is specifically inhibited by antisense RNA," *J. Cell Biol.*, 101:1094-1099, 1985.

Hermonat and Muzycska, "Use of adeno-associated virus as a mammalian DNA cloning vector: Transduction of neomycin resistance into mammalian tissue culture cells," *Proc. Nat'l Acad. Sci. USA*, 81:6466-6470, 1984.

Horwich et al., "Synthesis of hepadnavirus particles that contain replication-defective duck hepatitis B virus genomes in cultured HuH7 cells," *J. Virol.* 64(2):642-650, 1990.

Jansen et al., "bcl-2 antisense therapy chemosensitizes human melanoma in SCID mice," *Nature Medicine*, 4(2):232-234, 1998.

James, "Towards gene-inhibition therapy: a review of progress and prospects in the field of antiviral antisense nucleic acids and ribozymes," Antiviral Chemistry and Chemotherapy, 2(4):191-215, 1991.

Johnson et al., "Patterns of survival in patients with recurrent follicular lymphoma: a 20-year study from a single center," *J. Clin. Oncol.*, 13(1):140-147, 1995.

Klein et al., "High-velocity microprojectiles for delivering nucleic acids into living cells," *Nature*, 327:70-73, 1987.

Konopleva et al., "Inhibition of Bcl-2 with liposomal P-ethoxy antisense oligonucleotides induces apoptosisin the presence of high level of Bcl-Xl and is critically depending on baseline Bcl-2 levels in AML," *J. Amer. Soc. Hamagology*, 92(10)Suppl. 1, Part 1 of 2, Abstract No. 2100, 1998, abstract only.

Mann et al., "Construction of a retrovirus packaging mutant and its uses to produce helper-free defective retrovirus," *Cell*, 33:153-159, 1983.

McDonnell and Korsmeyer, "Progression from lymphoid hyperplasia to high-grade malignant lymphoma in mice transgenic for the t(14;18)," *Nature,* 349-:254-256, 1991.

Milner et al., "Selecting effective antisense reagents on combinational oligonucleotide arrays," *Nature,* 15:537-541, 1997.

Miyake et al., "Antisense Bcl-2 oligodeoxynucleotides inhibit progression to androgen-independence after castration in the Shionogi tumor model," *Cancer Res.,* 59:4030-4034, 1999.

Neilan et al., "An African Swine fever virus with similarity to the protooncogene *bcl-2* and the Epstein-Barr virus gene *BHRFI,*" *J. Virol.,* 67(7)4391-4394, 1993.

Nicolas and Rubenstein,"Retroviral vectors" *In: Vectors: A survey of molecular cloning vectors and their uses,* Rodriguez and Denhardt, (eds.), Stoneham: Butterworth, pp. 494-513, 1988.

Paskind et al., "Dependence of moloney murine leukemia virus production on cell growth," *Virology,* 67:242-248, 1975.

Palu et al., "In pursuit of new developments for gene therapy of human diseases," *Biotech.,* 68:1-13, 1999.

Pearson et al., "Identification of an Epstein-Barr virus early gene encoding a second component of the restricted early antigen complex," *Virology,* 160:151-161, 1987.

Pihl-Carey, "Disease drug fails in phase III," *BioWorld Today,* 10:1-2, 1999.

Potter et al., "Enhancer-dependent expression of human κ immunoglobulin genes introduced into mouse pre-B lymphocytes by electroporation," *Proc. Nat'l Acad. Sci. USA,* 81:7161-7165, 1984.

Ridgeway, "Mammalian expression vectors." *In:* Rodriguez RL, Denhardt DT, (ed.) Vectors: A survey of molecular cloning vectors and their uses. Stoneham: Butterworth, pp. 467-492, 1988.

Rippe et al. "DNA-mediated gene transfer into adult rat hepatocytes in primary culture," *Mol. Cell Biol.,* 10(2):689-695, 1990.

Stratford-Perricaudet and Perricaudet, "Gene transfer into animals: the promise of adenovirus," pp. 51-61, *In: Human Gene Transfer,* Eds, O. Cohen-Haguenauer and M. Boiron Editions John Libbey Exrotext, France, 1991.

Szoka and Papahadjopoulos, "Procedude for preparation of liposimes with large internal aqueous space and high capture by reverse-phase evaporation," *Proc. Nat'l Acad. Sci. U.S.A.* 75(9):4194-4198, 1978.

Temin, "Retrovirus vectors for gene transfer: Efficient integration into and expression of exogenous DNA in vertebrate cell genome," *In: Gene Transfer,* Kucherlapati (ed.), New York: Plenum Press, pp. 149-188, 1986.

Tur-Kaspa et al., "Use of electroporation to introduce biologically active foreign genes into primary rat hepatocytes," *Mol. Cell Biol.,* 6(2):716-718, 1986.

Verma et al., *Nature,* 389:238-243, 1997.

Wagner et al., "Antisense gene inhibition by pligonucleotides containing C5 propyne pyrimidines," *Science,* 260:1510-1513, 1993.

Wu and Wu, "Evidence for targeted gene delivery to Hep G2 hepatoma cells in vitro," *Biochemistry,* 27:887-892, 1988.

Wu and Wu, "Receptor-mediated in vitro gene transformations by a soluble DNA carrier system," *J. Biol. Chem.,* 262(10):4429-4432, 1987.

Yang et al., "In vivo and in vitro gene transfer to mammalian somatic cells by particle bombardment," *Proc. Nat'l Acad. Sci. USA,* 87:9568-9572, 1990.

Zelenin et al., "High-velocity mechanical DNA transfer of the chloramphenicolacetyl transferase gene into rodent liver, kidney and mammary gland cells in organ explants and in vivo," *FEBS Lett.,* 280(1):94-96, 1991.

Ziegler et al., "Induction of apoptosis in small-cell lung cancer cells by an antisense oligodeoxynucleotide targeting the Bcl-2 coding sequence," *J. Nat'l Cancer Institute,* 89(14):1027-1036, 1997.

Kitada et al., "Reversal of Chemoresistance of Lymphoma Cells by Antisense-Mediated Reduction of BCL-2 Gene Expression," *Antisense Research and Development,* 4:71 -79, 1994.

Tormo et al., "Apoptotic induction in transformed follicular lymphoma cells by Bcl-2 downregulation," *Leukemia & Lymphoma,* 30:367-379, 1998.

\* cited by examiner

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
cagcgtgcgc catccttc                                                 18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
acggtccgcc actccttccc                                               20
```

-continued

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
ctgaagggct tcttcc                                                    16

<210> SEQ ID NO 4
<211> LENGTH: 5086
<212> TYPE: DNA
<213> ORGANISM: Homo sapiens
<220> FEATURE:
<221> NAME/KEY: CDS
<222> LOCATION: (1459)..(2175)

<400> SEQUENCE: 4
gcgcccgccc ctccgcgccg cctgcccgcc cgcccgccgc gctccgcccc gccgctctcc      60 gtggcccgc cgcgctgccg ccgccgccgc tgccagcgaa ggtgccgggg ctccgggccc     120
tccctgccgg cggccgtcag cgctcggagc gaactgcgcg acgggaggtc cgggaggcga     180
ccgtagtcgc gccgccgcgc aggaccagga ggaggagaaa gggtgcgcag cccggaggcg     240
gggtgcgccg gtggggtgca gcggaagagg gggtccaggg gggagaactt cgtagcagtc     300 atcctttta ggaaagagg gaaaaaataa aaccctcccc caccacctcc ttctccccac     360
ccctcgccgc accacacaca gcgcgggctt ctagcgctcg gcaccggcgg gccaggcgcg     420
tcctgccttc atttatccag cagcttttcg gaaaatgcat ttgctgttcg gagtttaatc     480
agaagacgat tcctgcctcc gtccccggct ccttcatcgt cccatctccc ctgtctctct     540
cctggggagg cgtgaagcgg tcccgtggat agagattcat gcctgtgtcc gcgcgtgtgt     600
gcgcgcgtat aaattgccga gaaggggaaa acatcacagg acttctgcga ataccggact     660
gaaaattgta attcatctgc cgccgccgct gccaaaaaaa aactcgagct cttgagatct     720
ccggttggga ttcctgcgga ttgacatttc tgtgaagcag aagtctggga atcgatctgg     780
aaatcctcct aattttttact ccctctcccc ccgactcctg attcattggg aagtttcaaa     840
tcagctataa ctggagagtg ctgaagattg atgggatcgt tgccttatgc atttgttttg     900
gttttacaaa aaggaaactt gacagaggat catgctgtac ttaaaaaata caagtaagtc     960
tcgcacagga aattggttta atgtaacttt caatggaaac ctttgagatt ttttacttaa    1020
agtgcattcg agtaaattta atttccaggc agcttaatac attgttttta gccgtgttac    1080
ttgtagtgtg tatgccctgc tttcactcag tgtgtacagg gaaacgcacc tgatttttta    1140
cttattagtt tgttttttct ttaacctttc agcatcacag aggaagtaga ctgatattaa    1200
caatacttac taataataac gtgcctcatg aaataaagat ccgaaaggaa ttggaataaa    1260
aatttcctgc gtctcatgcc aagagggaaa caccagaatc aagtgttccg cgtgattgaa    1320 gacacccct cgtccaagaa tgcaaagcac atccaataaa atagctggat tataactcct    1380
cttctttctc tgggggccgt ggggtgggag ctggggcgag aggtgccgtt ggccccgtt    1440 gcttttcctc tgggaagg atg gcg cac gct ggg aga acg ggg tac gac aac      1491
                     Met Ala His Ala Gly Arg Thr Gly Tyr Asp Asn
                       1               5                  10 cgg gag ata gtg atg aag tac atc cat tat aag ctg tcg cag agg ggc      1539
Arg Glu Ile Val Met Lys Tyr Ile His Tyr Lys Leu Ser Gln Arg Gly -continued

```
                    15                  20                  25
tac gag tgg gat gcg gga gat gtg ggc gcc gcg ccc ccg ggg gcc gcc    1587
Tyr Glu Trp Asp Ala Gly Asp Val Gly Ala Ala Pro Pro Gly Ala Ala
             30                  35                  40 ccc gca ccg ggc atc ttc tcc tcc cag ccc ggg cac acg ccc cat cca    1635
Pro Ala Pro Gly Ile Phe Ser Ser Gln Pro Gly His Thr Pro His Pro
     45                  50                  55 gcc gca tcc cgc gac ccg gtc gcc agg acc tcg ccg ctg cag acc ccg    1683
Ala Ala Ser Arg Asp Pro Val Ala Arg Thr Ser Pro Leu Gln Thr Pro
 60                  65                  70                  75 gct gcc ccc ggc gcc gcc gcg ggg cct gcg ctc agc ccg gtg cca cct    1731
Ala Ala Pro Gly Ala Ala Ala Gly Pro Ala Leu Ser Pro Val Pro Pro
                 80                  85                  90 gtg gtc cac ctg gcc ctc cgc caa gcc ggc gac gac ttc tcc cgc cgc    1779
Val Val His Leu Ala Leu Arg Gln Ala Gly Asp Asp Phe Ser Arg Arg
             95                 100                 105 tac cgc ggc gac ttc gcc gag atg tcc agc cag ctg cac ctg acg ccc    1827
Tyr Arg Gly Asp Phe Ala Glu Met Ser Ser Gln Leu His Leu Thr Pro
         110                 115                 120 ttc acc gcg cgg gga cgc ttt gcc acg gtg gtg gag gag ctc ttc agg    1875
Phe Thr Ala Arg Gly Arg Phe Ala Thr Val Val Glu Glu Leu Phe Arg
     125                 130                 135 gac ggg gtg aac tgg ggg agg att gtg gcc ttc ttt gag ttc ggt ggg    1923
Asp Gly Val Asn Trp Gly Arg Ile Val Ala Phe Phe Glu Phe Gly Gly
140                 145                 150                 155 gtc atg tgt gtg gag agc gtc aac cgg gag atg tcg ccc ctg gtg gac    1971
Val Met Cys Val Glu Ser Val Asn Arg Glu Met Ser Pro Leu Val Asp
                 160                 165                 170 aac atc gcc ctg tgg atg act gag tac ctg aac cgg cac ctg cac acc    2019
Asn Ile Ala Leu Trp Met Thr Glu Tyr Leu Asn Arg His Leu His Thr
             175                 180                 185 tgg atc cag gat aac gga ggc tgg gat gcc ttt gtg gaa ctg tac ggc    2067
Trp Ile Gln Asp Asn Gly Gly Trp Asp Ala Phe Val Glu Leu Tyr Gly
         190                 195                 200 ccc agc atg cgg cct ctg ttt gat ttc tcc tgg ctg tct ctg aag act    2115
Pro Ser Met Arg Pro Leu Phe Asp Phe Ser Trp Leu Ser Leu Lys Thr
     205                 210                 215 ctg ctc agt ttg gcc ctg gtg gga gct tgc atc acc ctg ggt gcc tat    2163
Leu Leu Ser Leu Ala Leu Val Gly Ala Cys Ile Thr Leu Gly Ala Tyr
220                 225                 230                 235 ctg agc cac aag tgaagtcaac atgcctgccc caaacaaata tgcaaaaggt        2215
Leu Ser His Lys tcactaaagc agtagaaata atatgcattg tcagtgatgt accatgaaac aaagctgcag  2275
gctgtttaag aaaaaataac acacatataa acatcacaca cacagacaga cacacacaca  2335
cacaacaatt aacagtcttc aggcaaaacg tcgaatcagc tatttactgc caaagggaaa  2395
tatcatttat tttttacatt attaagaaaa aagatttatt tatttaagac agtcccatca  2455
aaactccgtc tttggaaatc cgaccactaa ttgccaaaca ccgcttcgtg tggctccacc  2515
tggatgttct gtgcctgtaa acatagattc gctttccatg ttgttggccg gatcaccatc  2575
tgaagagcag acggatggaa aaaggacctg atcattgggg aagctggctt tctggctgct  2635
ggaggctggg gagaaggtgt tcattcactt gcatttcttt gccctggggg cgtgatatta  2695
acagagggag ggttcccgtg gggggaagtc catgcctccc tggcctgaag aagagactct  2755
ttgcatatga ctcacatgat gcatacctgg tgggaggaaa agagttggga acttcagatg  2815
gacctagtac ccactgagat ttccacgccg aaggacagcg atgggaaaaa tgcccttaaa  2875
```

-continued

| | |
|---|---|
| tcataggaaa gtattttttt aagctaccaa ttgtgccgag aaaagcattt tagcaattta | 2935 |
| tacaatatca tccagtacct taaaccctga ttgtgtatat tcatatattt tggatacgca | 2995 |
| cccccccaact cccaatactg gctctgtctg agtaagaaac agaatcctct ggaacttgag | 3055 |
| gaagtgaaca tttcggtgac ttccgatcag gaaggctaga gttacccaga gcatcaggcc | 3115 |
| gccacaagtg cctgctttta ggagaccgaa gtccgcagaa cctacctgtg tcccagcttg | 3175 |
| gaggcctggt cctggaactg agccgggccc tcactggcct cctccaggga tgatcaacag | 3235 |
| ggtagtgtgg tctccgaatg tctggaagct gatggatgga gctcagaatt ccactgtcaa | 3295 |
| gaaagagcag tagaggggtg tggctgggcc tgtcaccctg ggccctcca ggtaggcccg | 3355 |
| ttttcacgtg gagcatagga gccacgaccc ttcttaagac atgtatcact gtagagggaa | 3415 |
| ggaacagagg ccctgggcct tcctatcaga aggacatggt gaaggctggg aacgtgagga | 3475 |
| gaggcaatgg ccacggccca ttttggctgt agcacatggc acgttggctg tgtggccttg | 3535 |
| gccacctgtg agtttaaagc aaggctttaa atgactttgg agagggtcac aaatcctaaa | 3595 |
| agaagcattg aagtgaggtg tcatggatta attgacccct gtctatggaa ttacatgtaa | 3655 |
| aacattatct tgtcactgta gtttggtttt atttgaaaac ctgacaaaaa aaagttcca | 3715 |
| ggtgtggaat atgggggtta tctgtacatc ctggggcatt aaaaaaaaat caatggtggg | 3775 |
| gaactataaa gaagtaacaa aagaagtgac atcttcagca aataaactag gaatttttt | 3835 |
| tttcttccag tttagaatca gccttgaaac attgatggaa taactctgtg gcattattgc | 3895 |
| attatatacc atttatctgt attaactttg gaatgtactc tgttcaatgt ttaatgctgt | 3955 |
| ggttgatatt tcgaaagctg ctttaaaaaa atacatgcat ctcagcgttt ttttgttttt | 4015 |
| aattgtattt agttatggcc tatacactat ttgtgagcaa aggtgatcgt tttctgtttg | 4075 |
| agatttttat ctcttgattc ttcaaaagca ttctgagaag gtgagataag ccctgagtct | 4135 |
| cagctaccta agaaaaacct ggatgtcact ggccactgag gagctttgtt tcaaccaagt | 4195 |
| catgtgcatt tccacgtcaa cagaattgtt tattgtgaca gttatatctg ttgtccctt | 4255 |
| gaccttgttt cttgaaggtt tcctcgtccc tgggcaattc cgcatttaat tcatggtatt | 4315 |
| caggattaca tgcatgtttg gttaaaccca tgagattcat tcagttaaaa atccagatgg | 4375 |
| cgaatgacca gcagattcaa atctatggtg gtttgacctt tagagagttg ctttacgtgg | 4435 |
| cctgtttcaa cacagaccca cccagagccc tcctgccctc cttccgcggg ggctttctca | 4495 |
| tggctgtcct tcagggtctt cctgaaatgc agtggtcgtt acgctccacc aagaaagcag | 4555 |
| gaaacctgtg gtatgaagcc agacctcccc ggcgggcctc agggaacaga atgatcagac | 4615 |
| ctttgaatga ttctaatttt taagcaaaat attatttat gaaaggttta cattgtcaaa | 4675 |
| gtgatgaata tggaatatcc aatcctgtgc tgctatcctg ccaaaatcat tttaatggag | 4735 |
| tcagtttgca gtatgctcca cgtggtaaga tcctccaagc tgctttagaa gtaacaatga | 4795 |
| agaacgtgga cgttttaat ataaagcctg ttttgtcttt tgttgttgtt caaacgggat | 4855 |
| tcacagagta tttgaaaaat gtatatatat taagaggtca cggggctaa ttgctagctg | 4915 |
| gctgcctttt gctgtggggt tttgttacct ggttttaata acagtaaatg tgcccagcct | 4975 |
| cttggcccca gaactgtaca gtattgtggc tgcacttgct ctaagagtag ttgatgttgc | 5035 |
| attttcctta ttgttaaaaa catgttagaa gcaatgaatg tatataaaag c | 5086 |

<210> SEQ ID NO 5
<211> LENGTH: 239
<212> TYPE: PRT
<213> ORGANISM: Homo sapiens

```
<400> SEQUENCE: 5

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65              70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235

<210> SEQ ID NO 6
<211> LENGTH: 911
<212> TYPE: DNA
<213> ORGANISM: Homo sapiens
<220> FEATURE:
<221> NAME/KEY: CDS
<222> LOCATION: (147)..(761)

<400> SEQUENCE: 6
tgattgaaga cacccctcg tccaagaatg caaagcacat ccaataaaat agctggatta      60
taactcctct tctttctctg ggggccgtgg ggtgggagct ggggcgagag gtgccgttgg    120 ccccgttgc ttttcctctg gaagg atg gcg cac gct ggg aga acg ggg tac      173
                          Met Ala His Ala Gly Arg Thr Gly Tyr
                          1               5 gac aac cgg gag ata gtg atg aag tac atc cat tat aag ctg tcg cag     221
Asp Asn Arg Glu Ile Val Met Lys Tyr Ile His Tyr Lys Leu Ser Gln
 10                  15                  20                  25 agg ggc tac gag tgg gat gcg gga gat gtg ggc gcc gcg ccc ccg ggg     269
Arg Gly Tyr Glu Trp Asp Ala Gly Asp Val Gly Ala Ala Pro Pro Gly
                 30                  35                  40 gcc gcc ccc gca ccg ggc atc ttc tcc tcc cag ccc ggg cac acg ccc     317
Ala Ala Pro Ala Pro Gly Ile Phe Ser Ser Gln Pro Gly His Thr Pro
             45                  50                  55
```

```
cat cca gcc gca tcc cgc gac ccg gtc gcc agg acc tcg ccg ctg cag     365
His Pro Ala Ala Ser Arg Asp Pro Val Ala Arg Thr Ser Pro Leu Gln
         60                  65                  70 acc ccg gct gcc ccc ggc gcc gcc gcg ggg cct gcg ctc agc ccg gtg     413
Thr Pro Ala Ala Pro Gly Ala Ala Ala Gly Pro Ala Leu Ser Pro Val
 75                  80                  85 cca cct gtg gtc cac ctg gcc ctc cgc caa gcc ggc gac gac ttc tcc     461
Pro Pro Val Val His Leu Ala Leu Arg Gln Ala Gly Asp Asp Phe Ser
 90                  95                 100                 105 cgc cgc tac cgc ggc gac ttc gcc gag atg tcc agc cag ctg cac ctg     509
Arg Arg Tyr Arg Gly Asp Phe Ala Glu Met Ser Ser Gln Leu His Leu
                110                 115                 120 acg ccc ttc acc gcg cgg gga cgc ttt gcc acg gtg gtg gag gag ctc     557
Thr Pro Phe Thr Ala Arg Gly Arg Phe Ala Thr Val Val Glu Glu Leu
             125                 130                 135 ttc agg gac ggg gtg aac tgg ggg agg att gtg gcc ttc ttt gag ttc     605
Phe Arg Asp Gly Val Asn Trp Gly Arg Ile Val Ala Phe Phe Glu Phe
         140                 145                 150 ggt ggg gtc atg tgt gtg gag agc gtc aac cgg gag atg tcg ccc ctg     653
Gly Gly Val Met Cys Val Glu Ser Val Asn Arg Glu Met Ser Pro Leu
 155                 160                 165 gtg gac aac atc gcc ctg tgg atg act gag tac ctg aac cgg cac ctg     701
Val Asp Asn Ile Ala Leu Trp Met Thr Glu Tyr Leu Asn Arg His Leu
170                 175                 180                 185 cac acc tgg atc cag gat aac gga ggc tgg gta ggt gca tct ggt gat     749
His Thr Trp Ile Gln Asp Asn Gly Gly Trp Val Gly Ala Ser Gly Asp
                190                 195                 200 gtg agt ctg ggc tgaggccaca ggtccgagat cggggttgg agtgcgggtg          801
Val Ser Leu Gly
             205 ggctcctggg caatgggagg ctgtggagcc ggcgaaataa aatcagagtt gttgcttccc   861 ggcgtgtccc tacctcctcc tctggacaaa gcgttcactc ccaacctgac              911

<210> SEQ ID NO 7
<211> LENGTH: 205
<212> TYPE: PRT
<213> ORGANISM: Homo sapiens

<400> SEQUENCE: 7

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
             35                  40                  45

Phe Ser Ser Gln Pro Gly His Thr Pro His Pro Ala Ala Ser Arg Asp
         50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Ala
                 85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140
```

```
Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Val Gly Ala Ser Gly Asp Val Ser Leu Gly
            195                 200                 205
```

INHIBITION OF BCL-2 PROTEIN EXPRESSION BY LIPOSOMAL ANTISENSE OLIGODEOXYNUCLEOTIDES

This application is a U.S. nationalization under 35 U.S.C. §371 of PCT/US97/18348, which claims priority to U.S. application Ser. No. 08/726,211, filed Oct. 4, 1996, now U.S. Pat. No. 6,977,244.

BACKGROUND OF THE INVENTION

A. Field of the Invention

The present invention relates to the field of cancer therapy, specifically, the treatment of Bcl-2 diseases. More particularly, these treatments involve the use of antisense oligodeoxynucleotides and liposomal formulations thereof.

B. Related Art

Bcl-2 has been linked to a wide variety of diseases such as hematologic malignancies, both leukemias and lymphomas, including follicular and nonfollicular lymphomas, chronic lymphocytic leukemia, and plasma cell dyscrasias (Campos et al., Blood, 84:595, 1994); solid tumors like those associated with breast, prostate and colon cancer; and immune disorders. One particular Bcl-2-related disease is Follicular non-Hodgkin Lymphoma (FL). FL is the most common lymphoid malignancy in Europe and the United States. Typically it is an indolent, low grade disease consisting of an accumulation of small, resting B cells. Although the response to chemotherapy is initially good, relapses are inevitable with the transformation to a more aggressive histological type and the development of drug resistance (Aisenberg, J. Clin. Oncol., 13:2656, 1995; Johnson et. al, J. Clin. Oncol., 13:140, 1995). In over 90% of FL patients, a t(14;18) translocation is found, which results in the juxtaposition of the bcl-2 gene from chromosome 18q21 with the immunoglobulin heavy chain gene locus on chromosome 14q323 (Tsujimoto et. al, Science, 229:1390, 1985; Graninger et. al, J. Clin. Invest., 80:1512, 1987). As a consequence, the bcl-2 gene is under the influence of immunoglobulin heavy chain enhancer, and the Bcl-2 protein is overexpressed (Bakhshi et. al, Cell, 41:899, 1985; Tsujimoto et. al, Oncogene, 2:3, 1987). Bcl-2 tumorigenic potential is related to its capacity of interfering with physiological death responses, thereby enhancing the longevity of the cell (Nuñez et. al, J. Immunol., 144:3602, 1990). The Bcl-2 protein blocks apoptotic stimuli such as growth factor deprivation, radiation, heat-shock, virus, and most of the chemotherapeutic agents (Reed, Hematol. Oncol. Clin. North Am., 9:451, 1995; Hockenbery et. al, Nature, 348:334, 1990). In bcl-2-Ig-transgenic mice, a polyclonal follicular lymphoproliferation consisting of an expansion of mature B lymphocytes is initially observed (McDonnell et. al, Cell, 57:79, 1989). Subsequently, a monoclonal high grade large immunoblastic type lymphomas develop with 50% of them presenting rearrangement of C-MYC. This suggests that a second genetic alteration is necessary for the development and progression of malignant lymphoma (McDonnell and Korsmeyer, Nature, 349:254, 1991).

Recently, an expanding family of Bcl-2-related proteins has been identified. This includes Bax, Bcl-$X_L$, Bcl-$X_S$, Bad, Bak, Mcl-1, A-1, and several open reading frames in DNA viruses (Oltvai et. al, Cell, 74:609, 1993; Boise et. al, Cell, 74:597, 1993; Yang et. al, Cell, 80:285, 1995; Chittenden et. al, Nature, 374:733, 1995; Kiefer et. al, Nature, 374: 736, 1995; Kozopas et. al Proc. Nat'l Acad. Sci. USA, 90:3516, 1993; Lin et. al, J. Immunol., 151:1979, 1993; Pearson et. al, Virology, 160:151, 1987; Neilan et. al, J. Virol., 67:4391, 1993). Membership in the Bcl-2 family of proteins is principally defined by homology within the BH1 and BH2 domains, which help regulate dimerization between the members (Sato et. al, Proc. Nat'l Acad. Sci. USA, 91:9238, 1994). Bax, which shares 21% amino-acid identity with Bcl-2, can bind to Bcl-2 protein and neutralize its ability to block cell death. Thus, the ratio of Bcl-2 to Bax is thought to determine the cell's susceptibility to death following an apoptotic stimulus (Oltvai et. al, 1993; Yin et. al, Nature, 369: 321, 1994).

Phosphodiester antisense oligodeoxynucleotides complementary to specific sequences of the translation-initiation site of Bcl-2 mRNA are able to inhibit the production of the Bcl-2 protein and the growth of t(14;18) translocation bearing cells (Kitada et. al, Antisense Res. Dev., 3:157, 1993). However, the therapeutic use of antisense oligonucleotides has been hampered by their low cellular uptake and their rapid degradation by nucleases and other serum or cellular components. Phosphorothioate oligonucleotides, which are resistant to nuclease degradation, were found to inhibit FL cell growth at concentrations 10 times lower than phosphodiester oligonucleotides (Reed et. al, Cancer Research, 50: 6565, 1990a; Cotter et. al, Oncogene, 9:3049, 1994). However, this approach suffers from low cellular uptake of the oligonucleotides. For example, Reed et. al had to use concentrations of greater than 25 µM of phosphorothioates to achieve 50% growth inhibitions of cell lines derived from B-cell lymphomas, such as 697 and Su-Dhl-4 cells. Liposomal incorporation has led to enhanced uptake of oligonucleotides into leukemic cells (Akhtar et. al, Nucleic Acids Res., 19:5551, 1991; Tari et. al, Blood, 84:601, 1994). The use of cationic lipids by Reed et. al to deliver phosphorothioate antisense oligonucleotides allowed them to reduce the concentration of oligonucleotides to 0.075 to 0.3 µM and still induce growth inhibition in Su-Dhl-4 cells.

There is still, however, a great need for methods and compositions for the treatment of Bcl-2 associated diseases such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders.

SUMMARY OF THE INVENTION

The present invention is designed to overcome the shortcomings of the prior art by providing improved compositions and methods for the treatment of Bcl-2 associated diseases, such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders, using novel antisense oligonucleotides to target specific nucleic acids in the cells of patients.

Thus, in one embodiment, there is provided a composition comprising a polynucleotide that hybridizes to a Bcl-2-encoding polynucleotide under intracellular conditions. Intracellular conditions as defined herein include monovalent cation at a concentration of approximately 160 mM (10 mM $Na^+$; 150 mM $K^+$) and a concentration of divalent cation of approximately 20 mM (18 mM $Mg^+$; 2 mM $Ca^{++}$). Intracellular conditions may also include a protein concentration, which would serve to decrease the volume of hybridization and, therefore, increase the effective concentration of nucleic acid species, of about 150 mg/ml.

The polynucleotides of the present invention may be oligonucleotides having a length of about 8-50 bases. The polynucleotides may be phosphodiester polynucleotides as found in nature, or they may preferably be derivatized polynucleotides or even polynucleotide analogs. Exemplary polymers would be p-ethoxy or methylphosphonate polynucleotides. Other analogs that may be used include, but are not limited to C-5 propyne pyrimidine polynucleotides (Wagner et al. *Science*, 260:1510-1513, 1993), or polynucleotides as described in U.S. Pat. No. 5,138,045 or European Patent Application EP 431,523, each incorporated herein by reference. Preferred analogs are nuclease resistant, have a high melting temperature, (bind tightly to RNA), and in certain embodiments preferred polynucleotides are hydrophobic for more efficient association with a lipid formulation such as a liposome.

In a further embodiment, the polynucleotide hybridizes to bcl-2 mRNA and preferable to the translation initiation site of Bcl-2 mRNA. It is understood however, that the antisense molecules of the present invention may hybridize to any area of the bcl-2 transcript that is effective to downregulate expression of the Bcl-2 protein. There are certain advantages to targeting the first open reading frame, and as stated, the transcription initiation site is particularly preferred. In certain specific embodiments, the polynucleotide may be an oligonucleotide having the sequence $5'$CAGCGTGCGC-CATCCTTC$3'$ (SEQ ID NO:1).

The polynucleotide preparation of the present invention is preferably associated with a lipid. A polynucleotide associated with a lipid may be described as encapsulated in the aqueous interior of a liposome, interspersed within the lipid bilayer of a liposome, attached to a liposome via a linking molecule that is associated with both the liposome and the polynucleotide, complexed with a lipid, dispersed in a solution containing a lipid, mixed with a lipid, combined with a lipid, contained as a suspension in a lipid, contained or complexed with a micelle, or otherwise associated with a lipid.

The term "lipids" as used in this specification and the claims denotes any form of both naturally occurring and synthetic lipids or liposomes. Lipids are fatty substances and are well-known by those of skill in the art. The lipids of the present invention are not limited to any particular structure in solution. For example, they may be present in a bilayer structure, as micelles, or with a "collapsed" structure. They may also simply be interspersed in a solution, possibly forming aggregates which are not uniform in either size or shape. The lipids are preferably neutral in net charge and may advantageously be comprised of the lipid dioleoylphosphatidylcholine, however other lipids such as other phosphatidylcholines, phosphatidylglycerols, and phosphatidylethanolamines may also be employed.

In yet another embodiment, there is provided a composition comprising a polynucleotide that hybridizes to a Bcl-2-encoding polynucleotide.

In still yet another embodiment, there is provided a composition comprising an expression construct that encodes a polynucleotide that hybridizes to a Bcl-2-encoding polynucleotide, wherein said first polynucleotide is under the control of a promoter that is active in eukaryotic cells.

This invention also comprises a method for inhibiting proliferation of a cancer cell comprising contacting said cancer cell with a composition comprising at least a polynucleotide that hybridizes to a Bcl-2-encoding nucleic acid. This method may be applied advantageously to a variety of cancer cells as shown in the Examples below. The methods of the invention are shown to be effective in cancer cells that overexpress or express high levels of bcl-2 and also express the Bax protein, as well as in cells in which translocation of p53 into the nucleus upon genotoxic damage is inhibited by bcl-2. Such cells would include, but are not limited to hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders. The composition may comprise a neutral lipid which is associated with the polynucleotide, such as a polynucleotide encapsulated in a liposome. In a specific embodiment, the contacting takes place in a patient, and in certain embodiments in a human patient. The composition may advantageously be delivered to a human patient in a volume of 0.50-10.0 ml per dose or in an amount of 5-30 mg polynucleotide per $m^2$. In a particular regimen, the composition is administered 3 times per week for 8 weeks. However, various dosages may be used as determined by an attending physician based on the particular disease, age and condition of the patient and other factors that may affect a physicians decision.

This invention relates to antisense technology that may be employed to treat Bcl-2-associated disease. In one embodiment it encompasses a composition comprising a polynucleotide that hybridizes to a Bcl-2-encoding polynucleotide and a neutral lipid associated with the polynucleotide, and preferably those that exclude cationic lipids. The polynucleotide may be an oligonucleotide having a length of between about 8 and about 50 bases. However, oligonucleotides of other lengths may also be useful. The polynucleotide may also hybridize to the translation initiation site of Bcl-2 mRNA. An example of a useful polynucleotide is an oligonucleotide comprising the sequence CAGCGTGCGCCATCCTTC (SEQ ID NO:1).

Compositions of the present invention also include compositions wherein liposomes are formed from the lipid. In some cases, it may be useful to have a composition in which the polynucleotide is encapsulated in the liposome. Lipids that are particularly useful in the present invention include phosphatidylcholines, phosphatidylglycerols, and phosphatidylethanolamines, one example being the lipid dioleoylphosphatidylcholine, although any acceptable neutral lipids may be used.

An embodiment of this invention is a composition comprising an expression construct that encodes a polynucleotide that hybridizes to a Bcl-2-encoding polynucleotide, wherein said polynucleotide is under the control of a promoter that is active in eukaryotic cells.

Another embodiment encompasses a method of inhibiting a Bcl-2-associated disease comprising obtaining a polynucleotide that hybridizes to a Bcl-2-encoding polynucleotide, mixing the polynucleotide with a neutral lipid to form a polynucleotide/lipid association, and administering said association to a cell. The cell may be a cancer cell, such as a follicular lymphoma cell. This method may employ a polynucleotide comprising an oligonucleotide having a length of between about 8 and about 50 bases. The lipid may comprise a liposome. If so, the liposome may further encapsulate the polynucleotide.

This embodiment also includes methods wherein the contacting takes place in an animal, such as a human. For example, the composition may be delivered to said human in a volume of 0.50-10.0 ml per dose or in an amount of from about 5 to about 30 mg polynucleotide per $m^2$. It may also be administered three times per week for eight weeks.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 4A: $1 \times 10^5$ Johnson cells/mL in 3 mL were treated with 3 and 4 μmol/L of L-bcl-2 or L-control oligos. After 3 days of culture, protein-containing lysates were prepared and 5 μg of total protein were subjected to SDS-PAGE and transferred to nitrocellulose membranes. Blots were cut into sections and incubated with antibodies specific for either Bcl-2 or Actin (left). To estimate the inhibition of bcl-2 protein, data were quantified by scanning densitometry and expressed as ratio of Bcl-2:Actin (right). L-bcl-2:(filled squares); L-control:(open circles).

FIG. 4B: $1 \times 10^5$ Jurkat cells/mL in 3 mL were treated with 3 and 4 μmol/L of L-bcl-2 or L-control oligonucleotides. After 3 days of culture, protein-containing lysates were prepared and 20 μg of total protein were subjected to SDS-PAGE and transferred to nitrocellulose membranes. Blots were cut into sections and incubated with antibodies specific for either Bcl-2 or Actin (left). To estimate the inhibition of bcl-2 protein, data were quantified by scanning densitometry and expressed as ratio of Bcl-2:Actin (right). L-bcl-2:(filled squares); L-control:(open circles).

FIG. 6A: $1 \times 10^5$ Johnson cells/mL in 3 mL were treated with 2, 3 and 4 μmol/L of L-bcl-2 or L-control oligos. After 3 days of culture, protein-containing lysates were subjected to SDS-PAGE and transferred to nitrocellulose membranes. Blots were cut into sections, and incubated with antibodies specific for either Bax or Actin. This experiment was made using the same lysates obtained in the experiment shown in FIG. 4A and FIG. 4B.

FIG. 6B: Data were quantified by scanning densitometry and expressed as ratio of Bcl-2:Bax. L-bcl-2:(filled squares); L-control oligo:(open circles).

FIG. 8A: Fluorescent photograph of Johnson cells dyed with the DNA-binding dye, acridine orange, after 3 days of incubation with 5 μmol/L of L-bcl-2 (right) or without liposomal oligonucleotides ("L-OS") (left).

FIG. 8B: Apoptotic index of Johnson cells treated with 4 and 5 μM of L-bcl-2 (dots), L-control oligo (horizontal) or empty liposomes (solid). Apoptotic index=(total no. of cells with apoptotic nuclei/total no. of cell counted)×100%.

FIG. 9A: Fluorescence microscopic evaluation of cell death induction following irradiation of LNCaP control and bcl-2 transfected cells (LNCaP-bcl-2). Control untreated (upper left), LNCaP-bcl-2 cells untreated (lower left), control cells 24 hours following 20 Gy γ-irradiation (upper right), and LNCaP-bcl-2 cells 24 hours following irradiation (lower right). Cells exhibited the characteristic features of apoptosis are commonly observed in control, but not LNCaP-bcl-2 cells following irradiation.

FIG. 9B: Flow cytometric analysis of cell death induction following 20 Gy of γ-irradiation in LNCaP cells. Apoptotic cells comprise approximately 30% of the LNCaP vector control cell population 8 hours following irradiation and <5% in the irradiated LNCaP-bcl-2 cells.

FIG. 10A: Western blot analysis of p53 protein induction and nuclear import following γ-irradiation in LNCaP control and LNCaP-bcl-2 cells. Subconfluent cultures of control LNCaP and LNCaP-bcl-2 cells were irradiated with 20Gy. Extracts of whole cells or nuclei isolated from whole cells were prepared 2 and 4 h after irradiation. Equivalent mounts of lysates were analyzed by immunoblotting with p53 antibody (Santa Cruz). Corresponding densitometric scans indicates that the mount of p53 protein induced following irradiation is approximately equivalent in whole cell extracts from LNCaP control and LNCaP-bcl-2 cells. However, nuclear accumulation of p53 protein is only observed in nuclei isolated from irradiated LNCaP control cells.

FIG. 10B: Confocal microscopic analysis of p53 subcellular localization following irradiation. LNCaP control (left) and LNCaP-bcl-2 (right) cells were irradiated with 20 Gy, fixed after 4 hours, and p53 protein imaged by scanning confocal laser microscopy. Nuclear localization of p53 protein is only observed in LNCaP control cells.

FIG. 10C: Bcl-2 inhibition of transcriptional activation by wt-p53. NIH3T3 cells were transfected with the effector wild type (P53 WT) or mutant p53 (P53 MUT) plasmid (10 μg), reporter plasmid P2mdm2-Luc (4 μg) and β-galactosidase (βgal) expression plasmid (3 μg) with or without the bcl-2 expression vector (BCL-2) (20 μg) using the calcium-phosphate method. Co-transfection with empty effector vector (VECTOR) served as a negative control. Data represent the fold increase in luciferase activity. Bcl-2 significantly inhibited the ability of wild type p53 protein to transactivate the mdm2 promoter (*p≦0.02).

FIG. 11A: Selective downregulation of bcl-2 protein in RKO colon cancer cells. Western blotting of whole cell extracts (40 μg) were analyzed by immunoblotting for bcl-2 protein. A graphic representation of the relative mount of bcl-2 protein after normalization for protein loading is shown. Treatment with antisense bcl-2 oligonucleotides, but not control oligonucleotides or empty liposomes, resulted in a reduction in the amount of bcl-2 protein.

FIG. 11B: Confocal microscopy of p53 protein in irradiated RKO cells treated with control oligonucleotides (top) or antisense-bcl-2 oligonucleotides (bottom). Significant nuclear localization of p53 protein following irradiation is observed only in antisense-bcl-2 treated RKO cells.

Figure 1A:
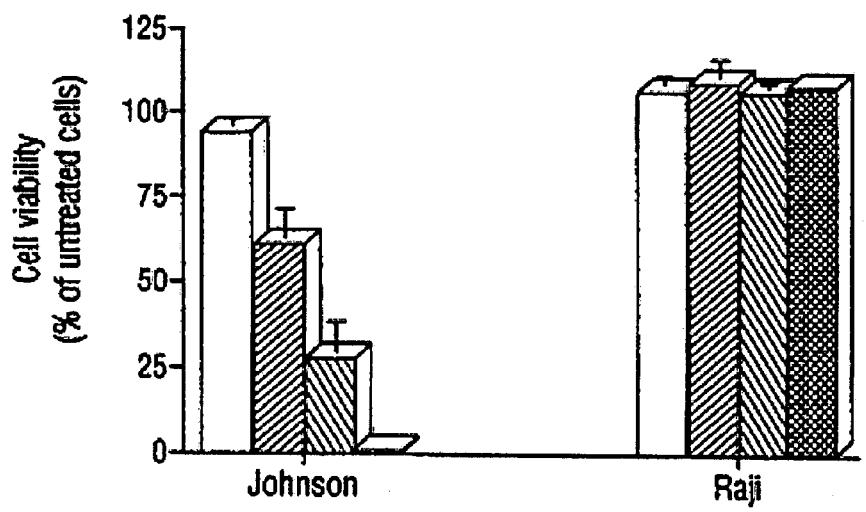
FIG. 1: Growth inhibition of lymphoid cells by liposomal-bcl-2-antisense oligonucleotides ("L-bcl-2"). Final concentrations of 3 μmol/L (dots), 4 μmol/L (horizontal), 5 μmol/L (vertical) and 6 μmol/L (diagonal) of L-bcl-2 were added to Johnson, Jurkat, Raji and Daudi cells. After 5 days, the viability of the tumoral cells was measured by alamarBlue dye. Viability was expressed as percent of untreated cells.

DETAILED DESCRIPTION OF THE PREFERRED EMBODIMENTS bcl-2 is an oncogene with tumorigenic potential due to its capacity to block programmed cell death. The present invention employs liposomal antisense oligodeoxynucleotides to inhibit the production of Bcl-2 so that tumor cells can regain the capacity to enter programmed cell death. The present invention may also be used to treat hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders, which are associated with Bcl-2 expression. Such diseases would include those involving cells that overexpress, or express a high level, of Bcl-2 and which also express Bax.

The present invention relates to antisense oligonucleotides and polynucleotides directed to portions of the bcl-2 gene and their use in the treatment of Bcl-2 related diseases. A specific type of cancer that may be treated by the methods of the present invention is FL. Over 90% of follicular lymphoma patients have a t(14;18) translocation which results in the translocation of the bcl-2 gene from its normal location in chromosome 18 to the immunoglobulin heavy chain gene locus on chromosome 14. In consequence, the bcl-2 gene is under the influence of the immunoglobulin heavy chain enhancer, and the Bcl-2 protein is overexpressed. Since bcl-2 is an oncogene with tumorigenic potential due to its capacity to block programmed cell death, a potential therapy for these follicular lymphomas is to inhibit the production of the Bcl-2 protein. The present invention hopes to succeed where other approaches have failed by incorporating stable, nuclease resistant antisense oligonucleotides specific for the first open reading frame, and more specifically, for the translation initiation site of the Bcl-2 mRNA, into neutral liposomes for delivery into the cell to inhibit the production of Bcl-2 protein.

In particular, it is contemplated that by using these antisense molecules, either alone or in conjunction with other antisense molecules, it is possible to effectively treat FL, and possibly other Bcl-2 cancers. For example, as shown herein, liposomal bcl-2 antisense oligonucleotides (L-bcl-2) inhibit the growth of FL cells and other cells which overexpress Bcl-2 protein. In the practice of the invention, the oligo- or polynucleotides themselves, or expression vectors encoding therefor, may be employed. The preferred method of delivering these nucleic acids is via liposomes, and in particular liposomes that are made of neutral lipids. The invention, in its various embodiments, is described in greater detail, below.

A. POLYNUCLEOTIDES AND OLIGONUCLEOTIDES

The term "antisense" is intended to refer to polynucleotide molecules complementary to a portion of a Bcl-2 RNA, or the DNA's corresponding thereto. "Complementary" polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences may offer certain advantages in some cases and does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

The intracellular concentration of monovalent cation is approximately 160 mM (10 mM Na$^+$; 150 mM K$^+$). The intracellular concentration of divalent cation is approximately 20 mM (18 mM Mg$^+$; 2 mM Ca$^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs for the present invention will include regions complementary to the mRNA start site. One can readily test such constructs simply by testing the constructs in vitro to determine whether levels of the target protein are affected. Such testing may be performed by transferring naked polynucleic acid molecules to the cell by various techniques known in the art, or by first associating the nucleic acid molecules with one or more lipids. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide for thirteen or fourteen positions out of fifteen. Naturally, sequences which are "completely complementary" or "full length complements" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

The polynucleotides according to the present invention may encode a bcl-2 gene or a portion of that gene that is sufficient to effect antisense inhibition of protein expression. The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the antisense polynucleotide may be produced synthetically.

It may be advantageous to combine portions of the genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

The DNA and protein sequences for Bcl-2 are published in literature by Tsujimoto and Croce, (*Proc. Natl. Acad. Sci. USA*, 83:5214, 1986) (SEQ ID NO:4, SEQ ID NO:5, SEQ ID NO:6, & SEQ ID NO:7) which is incorporated herein by reference. It is contemplated that natural variants of Bcl-2 exist that have different sequences than those disclosed herein. Thus, the present invention is not limited to use of the provided polynucleotide sequence for Bcl-2 but, rather, includes use of any naturally-occurring variants. Depending on the particular sequence of such variants, they may provide additional advantages in terms of target selectivity, i.e., avoid unwanted antisense inhibition of related transcripts. The present invention also encompasses chemically synthesized mutants of these sequences.

As stated above, although the antisense sequences may be full length genomic or cDNA copies, or large fragments thereof, they also may be shorter fragments, or "oligonucleotides," defined herein as polynucleotides of 50 or less bases. Although shorter oligomers (8-20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45 or 50 base pairs or larger may be used. While all or part of the gene sequence may be employed in the context of antisense construction, statistically, any sequence of 17 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993). In the practice of the invention, derivatized polynucleotides or phosphodiester analogues such as p-ethoxy or methyl phosphonate oligonucleotides may be used. Such polynucleotides may offer certain advantages such as nuclease resistance. It is a discovery of the present inventors that p-ethoxy oligonucleotides, which are hydrophobic are also advantageous in that they are more efficiently incorporated into liposomes.

As an alternative to targeted antisense delivery, targeted ribozymes may be used. The term "ribozyme" refers to an RNA-based enzyme capable of targeting and cleaving particular base sequences in both DNA and RNA. Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone.

Alternatively, the antisense oligo- and polynucleotides of the present invention may be provided as mRNA via transcription from expression constructs that carry nucleic acids encoding the oligo- or polynucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid encoding the inhibitory peptide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of various proteins. The use of other viral or mammalian cellular or bacterial phage promoters which are well-known in the art to achieve expression of peptides according to the present invention is contemplated as well, provided that the levels of expression are sufficient for a given purpose.

By employing a promoter with well-known properties, the level and pattern of expression of an antisense oligo- or polynucleotide can be optimized. Further, selection of a promoter that is regulated in response to specific physiologic signals can permit inducible expression of an inhibitory protein. For example, a nucleic acid under control of the human PAI-1 promoter results in expression inducible by tumor necrosis factor. Tables 1 and 2 list several elements/promoters which may be employed, in the context of the present invention, to regulate the expression of antisense constructs. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding an NF-IL6 inhibitory peptide in an expression construct (Table 1 and Table 2). Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

| PROMOTER | |
|---|---|
| Immunoglobulin Heavy Chain | c-HA-ras |
| Immunoglobulin Light Chain | Insulin |
| T-Cell Receptor | Neural Cell Adhesion Molecule (NCAM) |
| HLA DQ α and DQ β | α1-Antitrypsin |
| β-Interferon | H2B (TH2B) Histone |
| Interleukin-2 | Mouse or Type I Collagen |
| Interleukin-2 Receptor | Glucose-Regulated Proteins (GRP94 and GRP78) |
| MHC Class II 5 | Rat Growth Hormone |
| MHC Class II HLA-DRα | Human Serum Amyloid A (SAA) |
| β-Actin | Troponin I (TN I) |
| Muscle Creatine Kinase | Platelet-Derived Growth Factor |
| Prealbumin (Transthyretin) | Duchenne Muscular Dystrophy |
| Elastase I | SV40 |
| Metallothionein | Polyoma |
| Collagenase | Retroviruses |
| Albumin Gene | Papilloma Virus |
| α-Fetoprotein | Hepatitis B Virus |
| τ-Globin | Human Immunodeficiency Virus |
| β-Globin | Cytomegalovirus |
| c-fos | Gibbon Ape Leukemia Virus |

TABLE 2

| Element | Inducer |
|---|---|
| MT II | Phorbol Ester (TPA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester (TPA) |
| Tumor Necrosis Factor | PHA |
| Thyroid Stimulating Hormone α Gene | Thyroid Hormone |

In certain embodiments of this invention, the delivery of a nucleic acid in a cell may be identified in vitro or in vivo by including a marker in the expression construct. The marker would result in an identifiable change to the transfected cell permitting easy identification of expression. Enzymes such as herpes simplex virus thymidine kinase (tk) (eukaryotic) or chloramphenicol acetyltransferase (CAT) (prokaryotic) may be employed.

One also may include a polyadenylation signal to effect proper polyadenylation of the transcript. The nature of the polyadenylation signal is not believed to be crucial to the successful practice of the invention, and any such sequence may be employed. Examples include the SV40, globin or adenovirus polyadenylation signals. Also contemplated as an element of the expression cassette is a terminator. These elements can serve to enhance message levels and to minimize read through from the cassette into other sequences.

B. LIPID FORMULATIONS

In a preferred embodiment of the invention, the antisense oligo- or polynucleotides and expression vectors may be associated with a lipid. A polynucleotide associated with a lipid may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/oligonucleotide associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape. The lipids may be in the form of liposomes known in the art as multiple-lamellar vesicles, small or large unilamellar vesicles or other types of vesicles known in the art.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: Wu G. Wu C ed. Liver diseases, targeted diagnosis and therapy using specific receptors and ligands, New York: Marel Dekker, pp. 87-104, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Liposome-mediated polynucleotide delivery and expression of foreign DNA in vitro has been very successful. Wong et al., (*Gene*, 10:87-94, 1980) demonstrated the feasibility of liposome-mediated delivery and expression of foreign DNA in cultured chick embryo, HeLa and hepatoma cells. Nicolau et al., (*Methods Enzymol.*, 149:157-176, 1987) accomplished successful liposome-mediated gene transfer in rats after intravenous injection.

In certain embodiments of the invention, the lipid may be associated with a hemaglutinating virus (HVJ). This has been shown to facilitate fusion with the cell membrane and promote cell entry of liposome-encapsulated DNA (Kaneda et al., *Science*, 243:375-378, 1989). In other embodiments, the lipid may be complexed or employed in conjunction with nuclear non-histone chromosomal proteins (HMG-1) (Kato et al., *J. Biol. Chem.*, 266:3361-3364, 1991). In yet further embodiments, the lipid may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

Phospholipids are used for preparing the liposomes according to the present invention and can carry a net positive charge, a net negative charge or are neutral, with neutral phospholipids being the most preferred. Diacetyl phosphate is often employed to confer a negative charge on a liposome, and stearylamine to confer a positive charge on a liposome.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristoyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al., (*J. Mol. Biol.*, 13:238, 1965), the contents of which are incorporated herein by reference; the method of Gregoriadis, as described in *DRUG CARRIERS IN BIOLOGY AND MEDICINE*, G. Gregoriadis ed. (1979) pp. 287-341, the contents of which are incorporated herein by reference; the method of Deamer and Uster, (*LIPOSOMES*, M. Ostro ed. 1983), the contents of which are incorporated by reference; and the reverse-phase evaporation method as described by Szoka and Papahadjopoulos, (*Proc. Nat'l Acad. Sci. USA*. 75:4194-98 1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

P-ethoxy oligonucleotides, nuclease resistant analogues of phosphodiesters, are preferred because they are stable in serum and effectively transported into the cellular cytoplasm. In a preferred embodiment, the lipid dioleoylphosphatidylcholine is employed. However other lipids such as other phosphatidylcholines, phosphatidylglycerols, and phosphatidylethanolamines may also be useful. Nuclease-resistant oligonucleotides are mixed with lipids in the presence of excess t-butanol. The mixture is vortexed before being frozen in an acetone/dry ice bath. The frozen mixture is lyophilized and hydrated with Hepes-buffered saline (1 mM Hepes, 10 mM NaCl, pH 7.5) overnight, and then the liposomes are sonicated in a bath type sonicator for 10 to 15 min. The size of the liposomal-oligonucleotides typically ranges between 200-300 nm in diameter as determined by the submicron particle sizer autodilute model 370 (Nicomp, Santa Barbara, Calif.).

C. ALTERNATIVE DELIVERY SYSTEMS

Retroviruses. The retroviruses are a group of single-stranded RNA viruses characterized by an ability to convert their RNA to double-stranded DNA in infected cells by a process of reverse-transcription (Coffin, *In: Virology*, Fields et al. (eds.), New York: Raven Press, pp. 1437-1500, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a Bcl-2 antisense construct is inserted into the viral genome in the place of certain viral sequences to produce a virus that is replication-defective. In order to produce virions, a packaging cell line containing the gag, pol and env genes but without the LTR and Ψ components is constructed (Mann et al., *Cell*, 33:153-159, 1983). When a recombinant plasmid containing an inserted DNA, together with the retroviral LTR and Ψ sequences, is introduced into this cell line (by calcium phosphate precipitation for example), the Ψ sequence allows the RNA transcript of the recombinant plasmid to be packaged into viral particles, which are then secreted into the culture media (Nicolas and Rubenstein, *In: Vectors: A survey of molecular cloning vectors and their uses*, Rodriguez and Denhardt, (eds.), Stoneham: Butterworth, pp. 494-513, 1988; Temin, *In: Gene Transfer*, Kucherlapati (ed.), New York: Plenum Press, pp. 149-188, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al, *Virology*, 67:242-248, 1975).

Adenoviruses: Human adenoviruses are double-stranded DNA tumor viruses with genome sizes of approximate 36 kB. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, pp. 51-61, *In:*

*Human Gene Transfer*, Eds, O. Cohen-Haguenauer and M. Boiron Editions John Libbey Exrotext, France, 1991).

As only a small portion of the viral genome appears to be required in cis adenovirus-derived vectors offer excellent potential for the substitution of large DNA fragments when used in connection with cell lines such as 293 cells. Ad5-transformed human embryonic kidney cell lines (Graham et al., *J. Gen. Virol.*, 36:59-72, 1977) have been developed to provide the essential viral proteins in trans.

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, *Seminar in Virology*, 3:237-252, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Surprisingly persistent expression of transgenes following adenoviral infection has also been reported.

Other Viral Vectors as Expression Constructs. Other viral vectors may be employed as expression constructs in the present invention. Vectors derived from viruses such as vaccinia virus (Ridgeway, Stoneham: Butterworth, pp. 467-492, 1988; Baichwal and Sugden, In: Kucherlapati R, (ed.) Gene transfer. New York: Plenum Press, pp. 117-148, 1986; Coupar et al., *Gene*, 68:1-10, 1988) adeno-associated virus (AAV) (Ridgeway, 1988; Baichwal and Sugden, 1986; Hermonat and Muzycska, *Proc. Nat'l Acad. Sci. USA*, 81:6466-6470, 1984) and herpes viruses may be employed. They offer several attractive features for various mammalian cells (Friedman et al., *Genes Devel.* 3:1314, 1989; Ridgeway, 1988; Baichwal and Sugden, 1986; Coupar et al., 1988; Horwich et al., *J. Virol.* 64:642-650, 1990).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (*Hepatology*, 14:134A, 1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral Methods. Several non-viral methods for the transfer of expression vectors into cultured mammalian cells also are contemplated by the present invention. These include calcium phosphate precipitation (Graham and van der Eb, *Virology*, 52:456-467, 1973; Chen and Okayama, *Mol. Cell. Biol.*, 7:2745-2752, 1987; Rippe et al., *Mol. Cell. Biol.*, 10:689-695, 1990) DEAE-dextran (Gopal, *Mol. Cell. Biol.*, 5:1188-1190, 1985), electroporation (Tur-Kaspa et al., *Mol. Cell. Biol.*, 6:716-718, 1986; Potter et al., *Proc. Nat'l Acad. Sci. USA*, 81:7161-7165, 1984), direct microinjection (Harland and Weintraub, *J. Cell Biol.*, 101:1094-1099, 1985), DNA-loaded liposomes (Nicolau and Sene, *Biochem. Biophys. Acta*, 721:185-190, 1982; Fraley et al., *Proc. Nat'l Acad. Sci. USA*, 76:3348-3352, 1979) and lipofectamine-DNA complexes, cell sonication (Fecheimer et. al, *Proc. Nat'l Acad. Sci. USA*, 76:3348-52, 1979), gene bombardment using high velocity microprojectiles (Yang et al., *Proc. Nat'l Acad. Sci. USA*, 87:9568-9572, 1990), polycations and receptor-mediated transfection (Wu and Wu, *J. Biol. Chem.*, 262:4429-4432, 1987; Wu and Wu, *Biochemistry*, 27:887-892, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al., (*Proc. Nat'l Acad. Sci. USA*, 81:7529-7533, 1984) successfully injected polyomavirus DNA in the form of $CaPO_4$ precipitates into liver and spleen of adult and newborn mice demonstrating active viral replication and acute infection. Benvenisty and Neshif (*Proc. Nat'l Acad. Sci. USA*, 83:9551, 1986) also demonstrated that direct intraperitoneal injection of $CaPO_4$ precipitated plasmids results in expression of the transfected genes. It is envisioned that DNA encoding an Bcl-2 construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., *Nature*, 327:70-73, 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., *FEBS Lett.*, 280:94-96, 1991). This may require surgical exposure of the tissue or cells, to eliminate any intervening tissue between the gun and the target organ. DNA encoding a Bcl-2 construct may be delivered via this method.

D. PHARMACEUTICAL COMPOSITIONS AND ROUTES OF ADMINISTRATION

Where clinical application of liposomes containing antisense oligo- or polynucleotides or expression vectors is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the antisense expression vector encapsulated in a liposome as discussed above, further dispersed in pharmaceutically acceptable carrier or aqueous medium. Such compositions also are referred to as inocula. The phrases "pharmaceutically" or "pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for the treatment of skin cancers, to prevent chemotherapy-induced alopecia or other dermal hyperproliferative disorder. Alternatively, administration may be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting the dose include the physical and clinical state of the patient, the route of administration, the intended goal of treatment (alleviation of symptoms versus cure) and the potency, stability and toxicity of the particular therapeutic substance. For the instant application, it is envisioned that the amount of therapeutic peptide included in a unit dose will range from about 5-30 mg of polynucleotide.

E. EXAMPLES

Example 1

Synthesis of Oligonucleotides

Nuclease-resistant p-ethoxy oligonucleotides, non-ionic phosphodiester analogs, were purchased from Oligo Therapeutics (Willsonville, Oreg.). An oligonucleotide specific for the translation initiation site of human Bcl-2 mRNA: 5'CAGCGTGCGCCATCCTTC3' (SEQ ID NO:1) was used as antisense oligonucleotide. Two different control oligonucleotides were used: 5' ACGGTCCGCCACTCCTTCCC3' (SEQ ID NO:2) (scrambled version of Bcl-2 antisense oligonucleotide) and the random sequence 5'CTGAAGGGCTTCTTCC3' (SEQ ID NO:3).

Example 2

Preparation of liposomal oligonucleotides (L-OS)

P-ethoxy-oligonucleotides dissolved in distilled water were added to phospholipids (Avanti Polar Lipids, Alabaster, Ala.) in the presence of excess tert-butanol ($\geq$95% by volume). The mixture was frozen in a dry ice/acetone bath, lyophilized overnight and finally hydrated with HEPES buffered saline (1 mmol/L Hepes and 10 mmol/L NaCl) at a final oligonucleotide concentration of 0.1 mmol/L. Liposomal oligonucleotides (L-OS) were sonicated for 12 minutes in a bath-type sonicator. The average diameter of the particles was 100 nm±50 nm as determined in a NICOMP particle sizing system (Santa Barbara, Calif.).

Example 3

Oligonucleotide Inhibition of Protein Expression

Cell Lines

Johnson cells, a human transformed FL cell line bearing the t(14;18) translocation which overexpresses Bcl-2 protein, were used. Raji and Jurkat cells, a human Burkitt lymphoma cell line and a human acute T cell leukemia cell line, respectively, were also used. Both lines express the Bcl-2 protein but they lack the t(14;18) translocation. Daudi cells, a human Burkitt lymphoma cell line which does not express the Bcl-2 protein, was used as a negative control cell line. Johnson, Raji and Jurkat cells were grown in RPMI 1640 media (GIBCO, Grand Island, N.Y.) supplemented with 10% heat-inactivated fetal bovine serum (FBS). Daudi cells were grown in RPMI 1640 media supplemented with 20% heat-inactivated FBS.

Delivery of L-OS to cells

Ten thousand cells/well were seeded in a 96-well plate in 0.1 mL of the respective medium. Cells were incubated with L-OS at final concentration of 2 to 8 µmol/L at 37° C. in a 5% $CO_2$ incubator. Each study was done in triplicate and repeated at least 3 times.

Cell viability assay

The viability of the neoplastic cells was measured by the alamarBlue dye (Alamar, Sacramento, Calif.). After 5 days of incubation with L-OS, 40 µL of cells/well were aliquoted and added to 140 µL of fresh medium. Twenty µL of alamarBlue dye were added to each well. After incubation for 12 hours at 37° C., the plates were read directly on a microplate reader (Molecular Devices, Calif.) at 570 and 595 mm. The difference in absorbance between 570 and 595 nm was taken as the overall absorbance value of the cells. All experiments were analyzed by t-test in which the viabilities of the cells treated with the L-OS were compared with those of the untreated controls.

Western Blots for Bcl-2 and Bax protein

One hundred thousand cells/well were seeded in a 6-well plate in 3 mL of the respective medium, treated with 2, 3 and 4 µmol/L of L-OS and incubated at 37° C. Untreated cells were also maintained in culture. Samples were removed on day 3 after the addition of the L-OS and lysed in 100 µL of lysis buffer (1% Triton, 150 mmol/L NaCl and 25 mmol/L Tris pH 7.4) at 0° C. for 30 minutes. After centrifugation at 12,000×g for 10 minutes, the supernatants were recovered and normalized for total protein content (5 µg/lane of Johnson cells lysate and 20 µg/lane of Jurkat cells lysate for Bcl-2 analysis, and 25 µg/lane of Johnson cells for Bax analysis). The lysates were mixed with sample buffer containing 1% of sodium dodecyl sulfate (SDS) and 1% 2-β-mercaptoethanol and boiled for 5 minutes. SDS-PAGE was run on 10% polyacrylamide gels, electrophoretically transferred to nitrocellulose membranes and blocked in 10% non-fat dry milk. Filters were cut in 2 portions: the bottom section was incubated with the 6C8 hamster anti-human-Bcl-2 monoclonal antibody or rabbit anti-human-Bax polyclonal antibody (Hockenbery et. al, *Nature,* 348:334, 1990), and the top section was incubated with mouse anti-actin monoclonal antibody (Amersham) at room temperature for 2 hours. After washing and incubation with a peroxidase-labeled antihamster (Kirkegaar & Perry laboratories), anti-rabbit (Santa Cruz) or antimouse (Amersham) secondary antibody, blots were developed by enhanced chemiluminescence system (ECL, Amersham). To estimate the inhibition of Bcl-2 protein and the ratio of Bcl-2/Bax proteins, densitometric scans were performed on western blots on a Gilford Response Gel Scanner (CIBA Corning, Medfield, Mass.). Area integration of absorbance peaks at 500 nm was used to determine the ratio of Bcl-2:Actin and Bcl-2:Bax proteins.

Analysis of apoptosis

To qualitatively determine the internucleosomal DNA cleavage associated with apoptosis, DNA fragmentation analysis by agarose gel electrophoresis was performed (Duke et. al In: Coligan et. al (eds) Current protocols in immunology, vol 1., New York: John Wiley & sons, p 3.17.1, 1991). In brief, $1\times10^6$ Johnson cells were cultured in 10 mL of medium in a 75 sq. cm tissue culture flask, treated with 4 µmol/L of L-OS, and incubated at 37° C. Untreated cells were also maintained in culture. Samples were removed on day 3 after treatment, washed in PBS and pellet by centrifuging 10 minutes at 200×g. The pellets were lysed in 0.5 mL of lysis buffer (10 mmol/L Tris pH 7.4, 1 mmol/L EDTA pH 8.0 and 0.2% Triton X-100) and fragmented DNA were separated from intact chromatin by microcentrifuging for 10 minutes at 13,000×g. DNA of the supernatants was precipitated in 0.7 mL ice-cold isopropanol overnight at −20° C., resuspended in 30 µL of TE buffer (10 mmol/L Tris pH 7.4, 1 mmol/L EDTA pH 8.0) and incubated in 10 µL of RNase (10 µg/mL solution) at 60° C. for 1 hour. Twenty µL of sample per well were electrophoresed on a 2% agarose gel and visualized by ethidium bromide staining.

To quantitatively determine the extent of apoptosis, the fluorescent DNA-binding dye acridine orange (Duke et. al, 1991) was used. Briefly, 5 µmol/L final concentration of L-OS were added to $1\times10^5$ cells/well plated in a 24-well plate in 1 mL of medium. After 3 days of incubation at 37° C., the cells were washed with PBS and resuspended at $1\times10^6$ cells/mL. Twenty-five µL of cell suspension were mixed with 1 µL of acridine orange dye (100 µg/mL, Sigma Chemicals, St. Louis, Mo.) and observed in a fluorescent microscope. The percentage of apoptotic cells (apoptotic index) was obtained using a hemocytometer. Apoptotic index=(total no. of cells with apoptotic nuclei/total no. of cells counted)×100%.

Figure 1B:
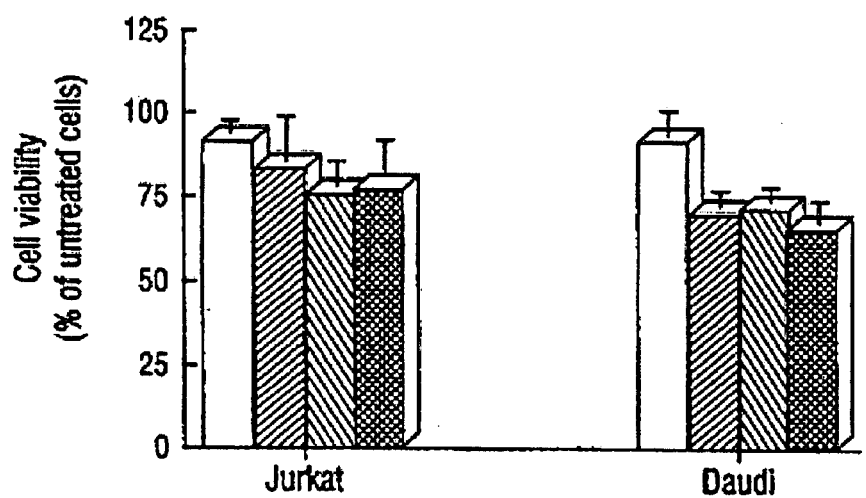

Effect of L-bcl-2-Antisense Oligonucleotides ("L-bcl-2") on Lymphoma Cell Growth Five days after the addition of L-bcl-2 to the cells, the viability of tumoral cells was assessed. Cell growth was inhibited in a concentration-dependent manner in Johnson cells, which bear the t(14;18) translocation and express very high levels of Bcl-2. A concentration of 6 µmol/L L-bcl-2 resulted in complete loss of viability of Johnson cells within 5 days (FIG. 1). Similar dose-dependent decrease in cell viabilities could be seen in three separate studies. In contrast, after treatment with 6 µmol/L( )L-bcl-2, the viabilities of Jurkat, Raji and Daudi cells decreased by only 23%, 0% and 35%, respectively (FIG. 1).

Figure 2A:
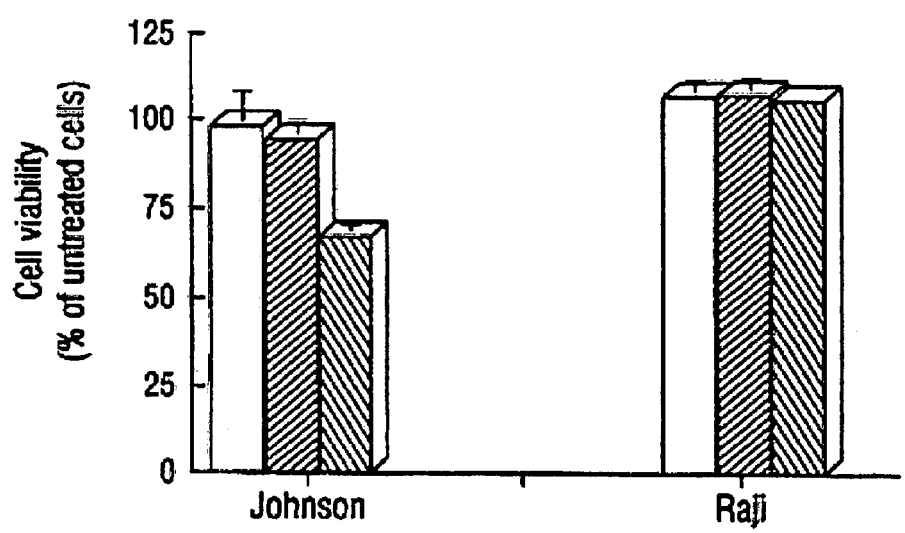
FIG. 2: Non-specific toxicity in lymphoid cells at 6 μmol/L of liposomal oligonucleotides. Empty liposomes (diagonal) and two different liposomal control oligonucleotides ("L-control oligos") (gray, black) were added to Johnson, Jurkat, Raji and Daudi cells at 6 μmol/L final concentration. After 5 days, the viability of the tumoral cells was measured by alamar blue dye. Viability was expressed as percent of untreated cells.
Figure 2B:
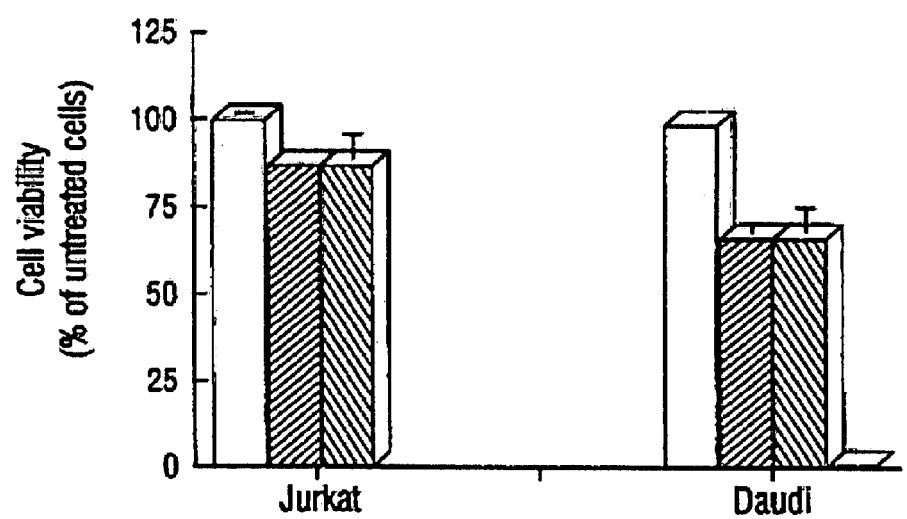

Effect of Liposomal Control Oligonucleotides (L-Control Oligos) on Lymphoma Cell Growth Two control oligonucleotides were used to determine the specificity of the inhibition observed. When L-control oligos or empty liposomes were added to Johnson cells, cell growth inhibition was not observed. Jurkat, Raji and Daudi cells were also treated with L-control oligos and empty liposomes. Non-specific toxicity could be observed when greater than 6 µmol/L of L-OS were used, but not with empty liposomes (FIG. 2).

Selective Inhibition of Bcl-2 Protein by L-bcl-2-Antisense Oligonucleotides

Figure 3:
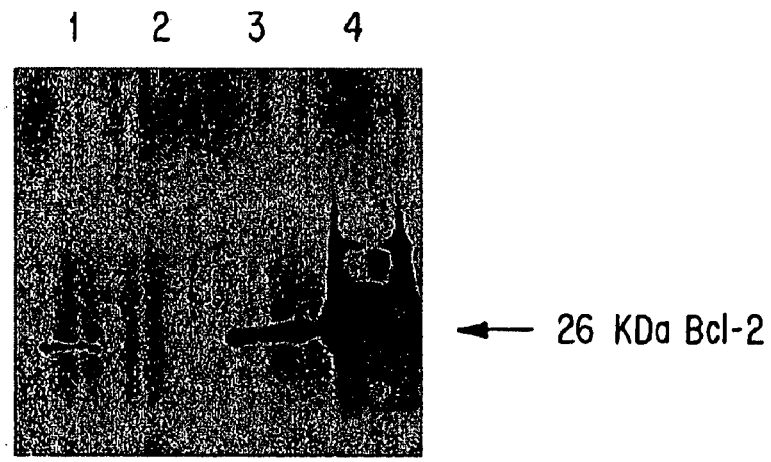
FIG. 3: Western blot analysis of Bcl-2 protein in the four cell lines. Johnson, Jurkat, Daudi and Raji cells were lysed in sample buffer and normalized for total protein content. Twenty-five grams of total protein was loaded in each lane. The membranes were incubated with hamster anti-human bcl-2 monoclonal antibody. In Johnson cells, a cell line bearing the t(14;18) translocation, overexpression of Bcl-2 protein is observed. In Jurkat and Raji cells, which lack the t(14;18) translocation, expression of Bcl-2 is low. In Daudi cells, Bcl-2 expression is not observed.

In order to determine whether the cytotoxic effect of L-bcl-2 in Johnson cells was caused by a decrease in Bcl-2 protein, the Bcl-2 protein expression in these cells after treatment with L-bcl-2 as well as the effects of L-bcl-2 in the other cell lines which overexpress Bcl-2 protein (FIG. 3). was also determined.

When Johnson cells were treated with 2, 3 and 4 mmol/L of L-bcl-2, the ratios of Bcl-2/Actin protein were inhibited by 28, 57 and 64%, respectively. Bcl-2 protein expression was not inhibited in cells treated with the same doses of L-control oligos.

Figure 4A:
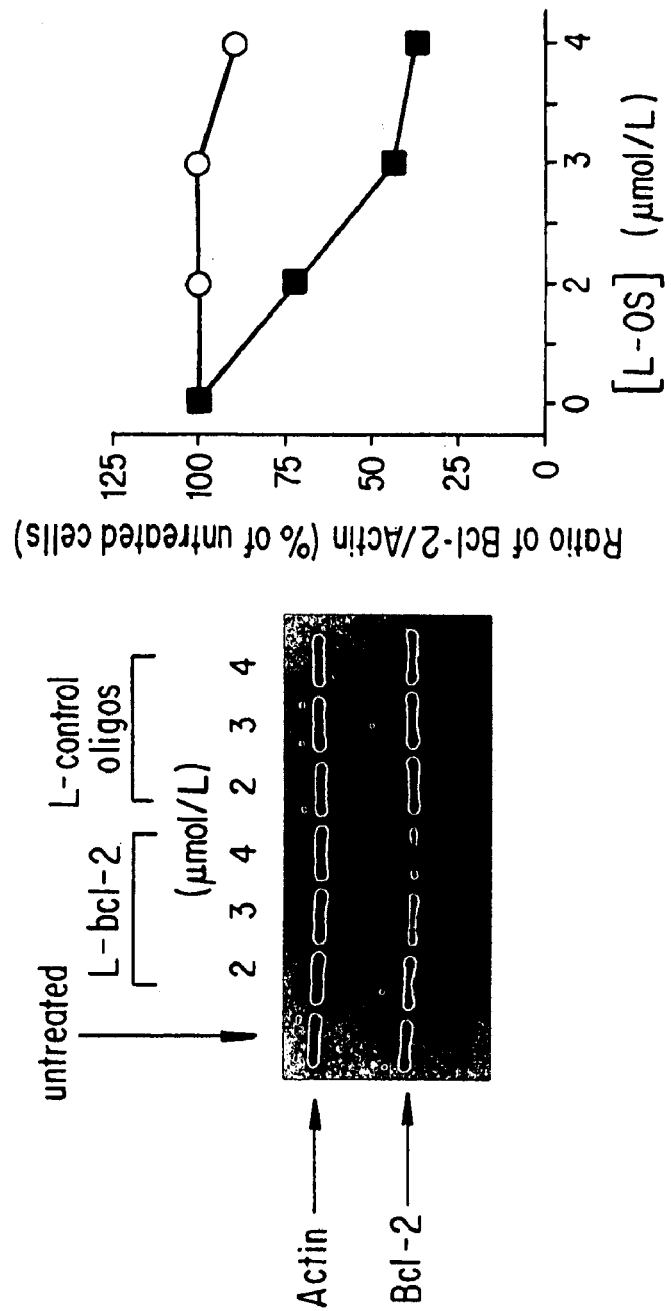
FIG. 4A & FIG. 4B: Specific inhibition of Bcl-2 protein in Johnson and Jurkat cells by L-bcl-2.
Figure 4B:
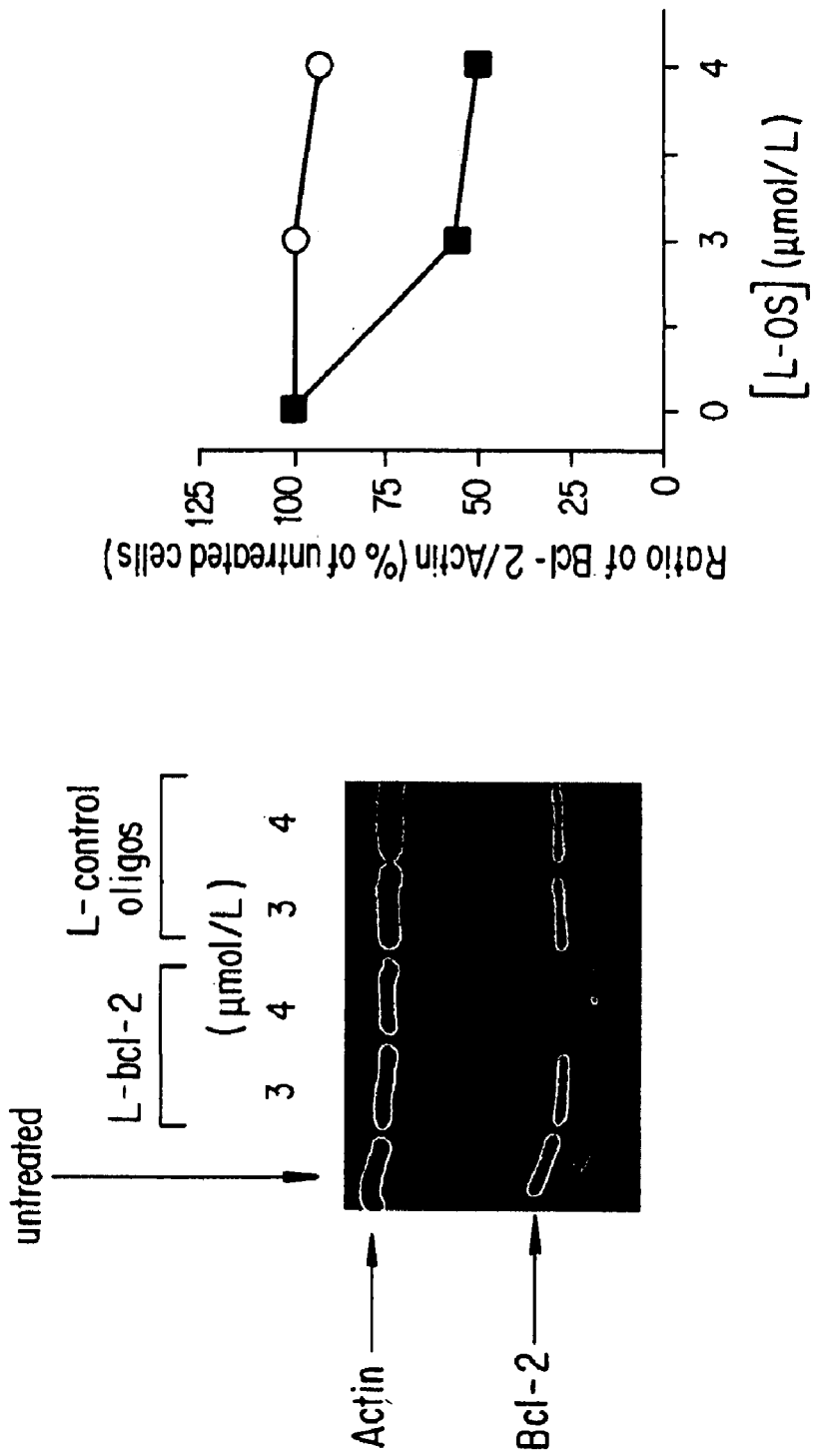

When Jurkat cells were treated with 3 and 4 mmol/L of L-bcl-2, the ratios of Bcl-2/Actin protein were inhibited by 44% and 50%, respectively. Bcl-2 protein was not significantly inhibited when the same doses of L-control oligos were used (FIG. 4).

Figure 5:
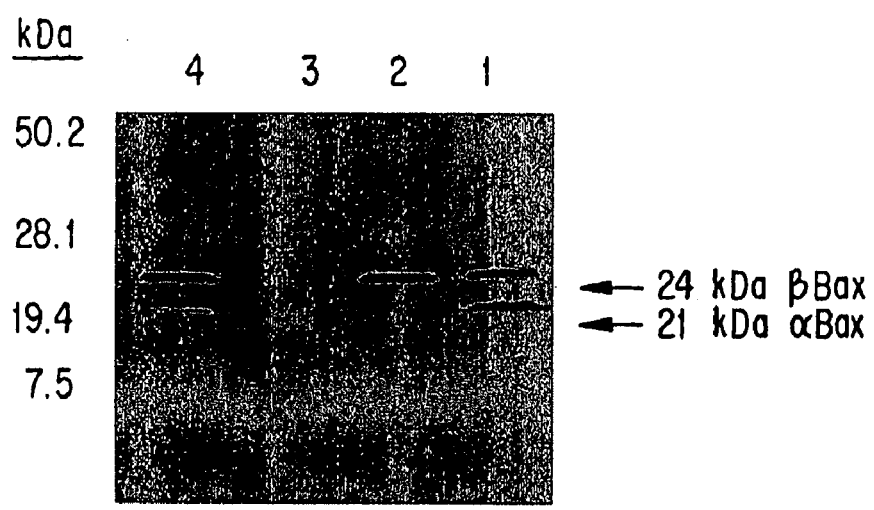
FIG. 5: Western blot analysis of Bax protein in the four cell lines. Johnson, Jurkat, Daudi and Raji cells were lysed in sample buffer and normalized for total protein content. Fifty μg of total protein was loaded in each lane. The membranes were incubated with rabbit anti-human Bax polyclonal antibody.
Figure 6A:
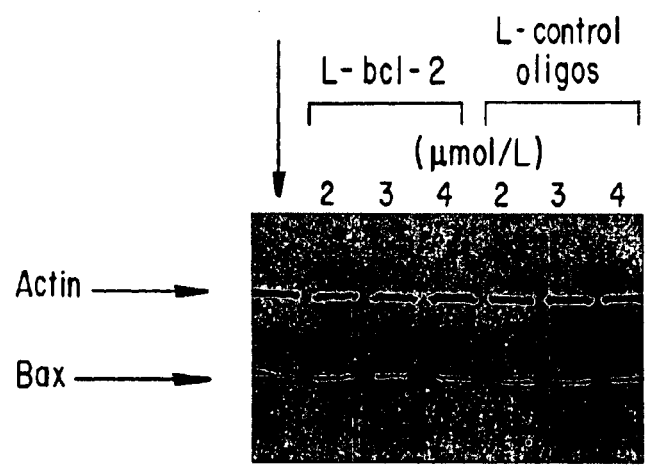
FIG. 6A & FIG. 6B: Bcl-2/Bax ratio decreases in Johnson cells by L-bcl-2.
Figure 6B:
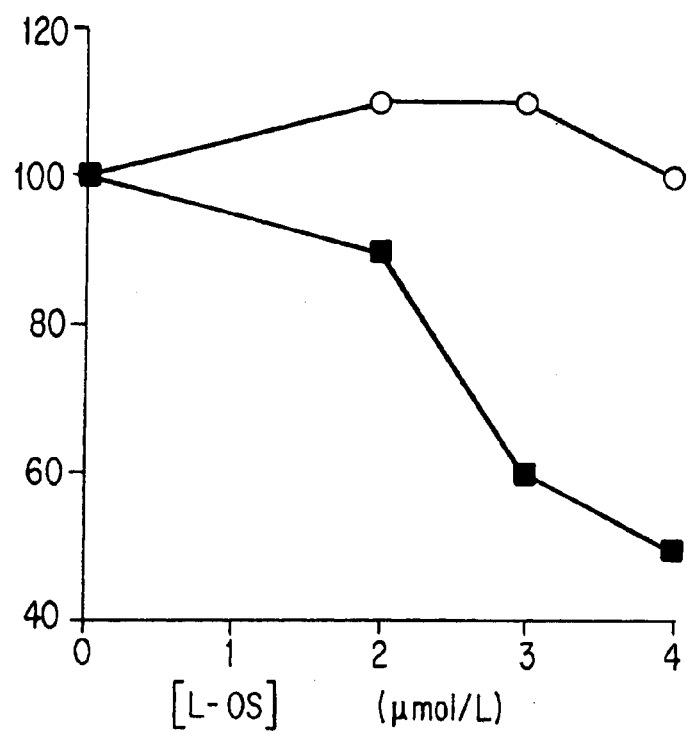

The ratios of Bcl-2/Bax protein in Johnson and Jurkat cells before and after treatment with L-bcl-2 and L-control oligos were also determined. Johnson, Raji and Daudi cells expressed Bax protein but Jurkat cells did not express (FIG. 5). When Johnson cells were treated with 2, 3 and 4 mmol/L of L-bcl-2, the ratio of Bax/Actin was not modified, but the ratio of Bcl-2/Bax decreased by 10%, 40% and 50%, respectively. These protein ratios were unmodified after treatment with the same doses of L-control oligos (FIG. 6).

Inhibition of Bcl-2 Protein Leads to Apoptosis in the FL Cells

Figure 7:
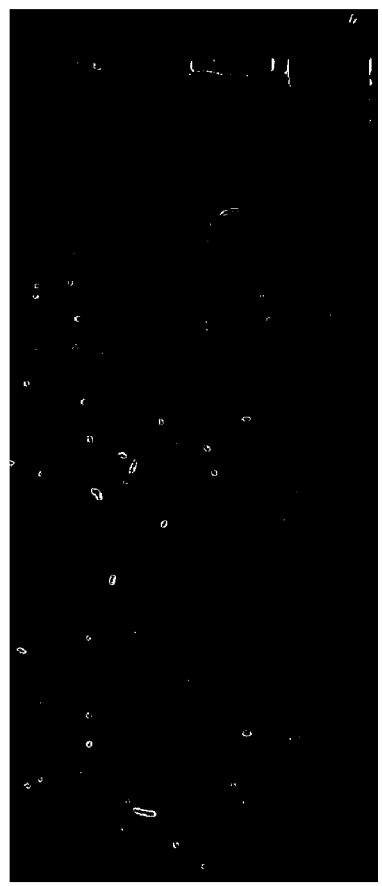
FIG. 7: DNA fragmentation in Johnson cells incubated with L-Bcl-2. Johnson cells were incubated with 4 μmol/L of L-bcl-2 and two L-control oligos. After 3 days of incubation, DNA was extracted, electrophoresed through a 2% agarose gel and stained with ethidium bromide. Lanes1, untreated cells; lane 2, cells treated with L-control (scrambled) oligo; lane 3, cells treated with L-control (random) oligo; lane 4, cells treated with L-bcl-2.
Figure 8A:
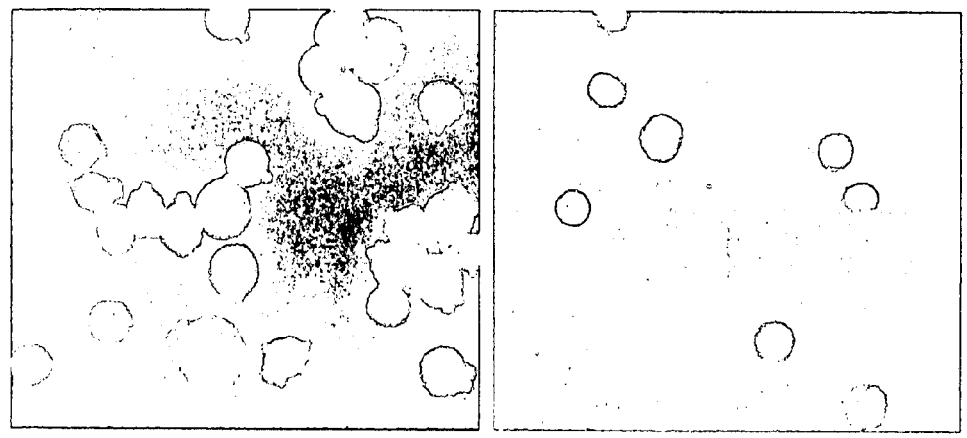
FIG. 8A & FIG. 8B: Apoptotic Johnson cells incubated with L-bcl-2.
Figure 8B:
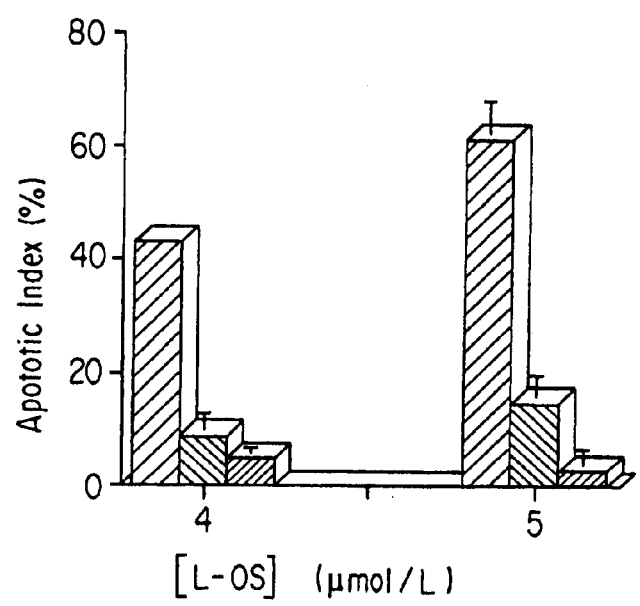

Whether the growth inhibitory effects seen in Johnson cells may be related to induction of apoptosis was also studied. After 3 days of incubation with L-bcl-2, the typical internucleosomal DNA degradation pattern was observed, whereas cells incubated with L-control oligos did not show the internucleosomal DNA pattern (FIG. 7). Subsequently, the quantity of apoptosis by acridine orange was assessed. After 3 days of exposure to 4 and 5 µmol/L of L-bcl-2, apoptotic cells were evident. The apoptotic index of untreated Johnson cells was 3% while that of Johnson cells treated with 4 and 5 µmol/L of L-bcl-2 were 43% and 61%, respectively. Significant increase in apoptotic index was not seen in cells treated with liposomal control oligonucleotides or empty liposomes (FIG. 8).

L-bcl-2 Selectively Downregulates the Expression of Bcl-2 Protein and Cell Growth in a Dose-Dependent Manner The inhibition in cell growth was seen only in the FL cell line which bears the t(14;18) translocation, while cell growth inhibition was not seen in cell lines that lack the Bcl-2 expression (Daudi cells) or the t(14;18) translocation (Raji and Jurkat cells). There was no non-specific toxicity in Johnson cells exposed to two different control oligonucleotides. The growth inhibitory effects could be observed starting at a concentration of 3 µmol/L of L-bcl-2, and the inhibitory effects were maximal at 6 µmol/L concentration. One of the mechanisms by which L-bcl-2 exerts growth inhibition in Johnson cells might be through induction of apoptosis, since treated cells showed a typical DNA internucleosomal degradation pattern, and an increased apoptotic index as measured by acridine orange. By day 3, 61% of Johnson cells treated with 5 µmol/L of L-bcl-2 were in apoptosis as compared with 15% of cells treated with L-control oligos. Apoptosis was not observed in the other cell types.

Thus, the inhibition of Bcl-2 protein leads to cell growth inhibition in cells that are dependent on the presence of Bcl-2 protein for maintaining viability. Gene transfer experiments have provided evidence that Bcl-2 plays an important role in maintaining lymphoid cell survival in vitro, although other autocrine growth factors may also be involved (Vaux el. al, *Nature* (London), 355: 440, 1988; Reed et al., *Proc. Nat'l Acad. Sci. USA,* 87:3660, 1990b; Blagosklonny and Neckers, *Eur. Cytokine Network,* 6:21, 1995). Using phosphorothioate antisense oligonucleotides, Cotter and coworkers observed growth inhibition in DoHH2 cell line which has the t(14;18) translocation and overexpress Bcl-2 protein, but not in FC11 cell line which overexpresses Bcl-2 protein without the t(14;18) translocation (Cotter et. al, 1994). Cells that overexpress Bcl-2 and lack the t(14;18) translocation may need an apoptotic stimulus, like growth factor deprivation or treatment with chemotherapeutic drugs, to be driven into apoptosis and growth arrest (Reed, 1995). Antisense oligonucleotides may be used to reverse the chemotherapeutic resistance of those cells that also overexpress high levels of Bcl-2 without the t(14;18) translocation (Kitada et al., *Antisense Res. Dev.,* 4:71, 1994). It is understood that such a combination of L-Bcl-2 of the present disclosure with an apoptotic stimulus would be encompassed by the spirit and scope of the appended claims.

Bax, a promoter of apoptotic cell death, may be a common partner involved in heterodimerization and regulation of other Bcl-2 family member functions (Sedlak et. al, *Proc. Nat'l Acad. Sci. USA,* 92:7834, 1995). It has been suggested that the equilibrium in the formation of Bcl-2:Bax heterodimers and Bax:Bax homodimers appears to be central in the molecular regulation of apoptosis (Yin et. al, 1994). Moreover, in a recent study, the ratio of Bcl-2:Bax correlated with cell death in IL-3-dependent FL5.12 cells. When approximately half or more of Bax was heterodimerized with Bcl-2, apoptosis was inhibited (Yang et. al, 1995). The apoptotic death observed in Johnson cells, after incubation with L-bcl-2, could be due to decrease in Bcl-2:Bax ratio and formation of more Bax:Bax homodimers.

Another explanation is that other oncogenes and tumor suppressor genes such as C-MYC and p53 may be involved in the survival of the other cell lines. C-MYC, for example, is typically expressed in Burkitt lymphomas and in some transformed FL (McDonnell and Korsmeyer, 1991). Mutations of p53 gene, a suppressor gene involved in numerous human tumors, may also be involved in these cell lines; p53 gene encodes a DNA-binding protein that functions at least in part as a transcription factor to induce cell cycle arrest and apoptosis by upregulation of Bax (Vogelstein and Kinzler, *Cell,* 70:523, 1992; Miyashita et. al *Oncogene,* 9:1799, 1994; Miyashita and Reed, *Cell,* 80:293, 1995). Probably, inhibition of Bcl-2 expression alone is not enough to induce apoptosis and growth inhibition in cells other than those cells with a high expression level of Bcl-2 such as those with a t(14;18) translocation. However, as described herein, a decrease in the ratio of Bcl-2/Bax by L-bcl-2 forms the basis for a molecular approach to follicular lymphoma therapy as well as other Bcl-2 diseases in cells in which Bax is expressed.

Example 4

Bcl-2 Regulation p53 Nuclear Import

Figure 9A:
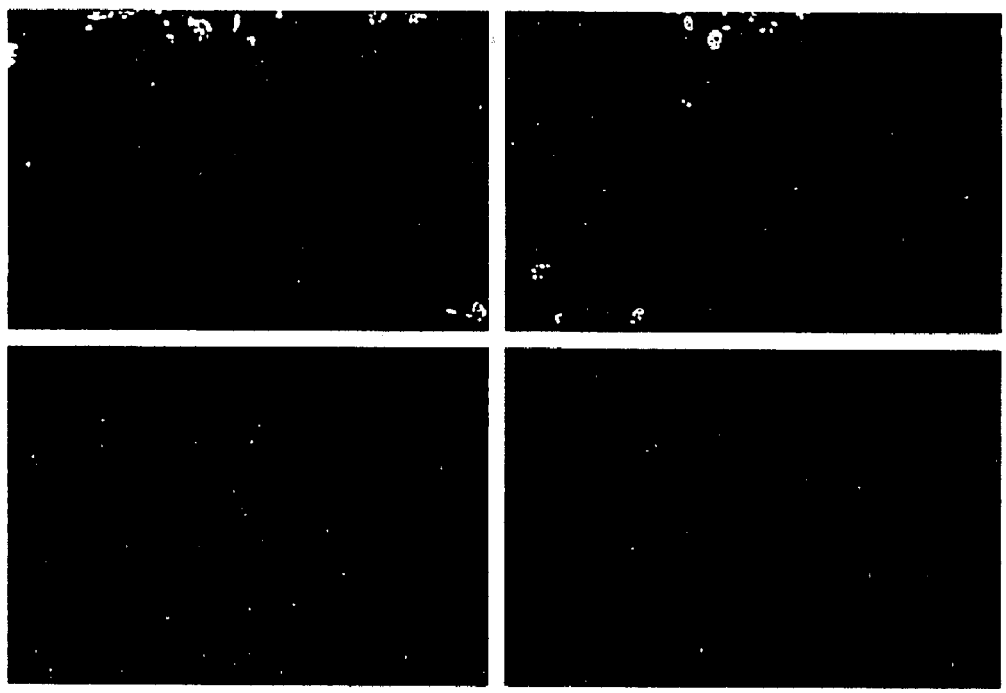
FIG. 9A & FIG. 9B: Evaluation of cell death following irradiation of LNCaP control and bcl-2 transfected cells.
Figure 9B:
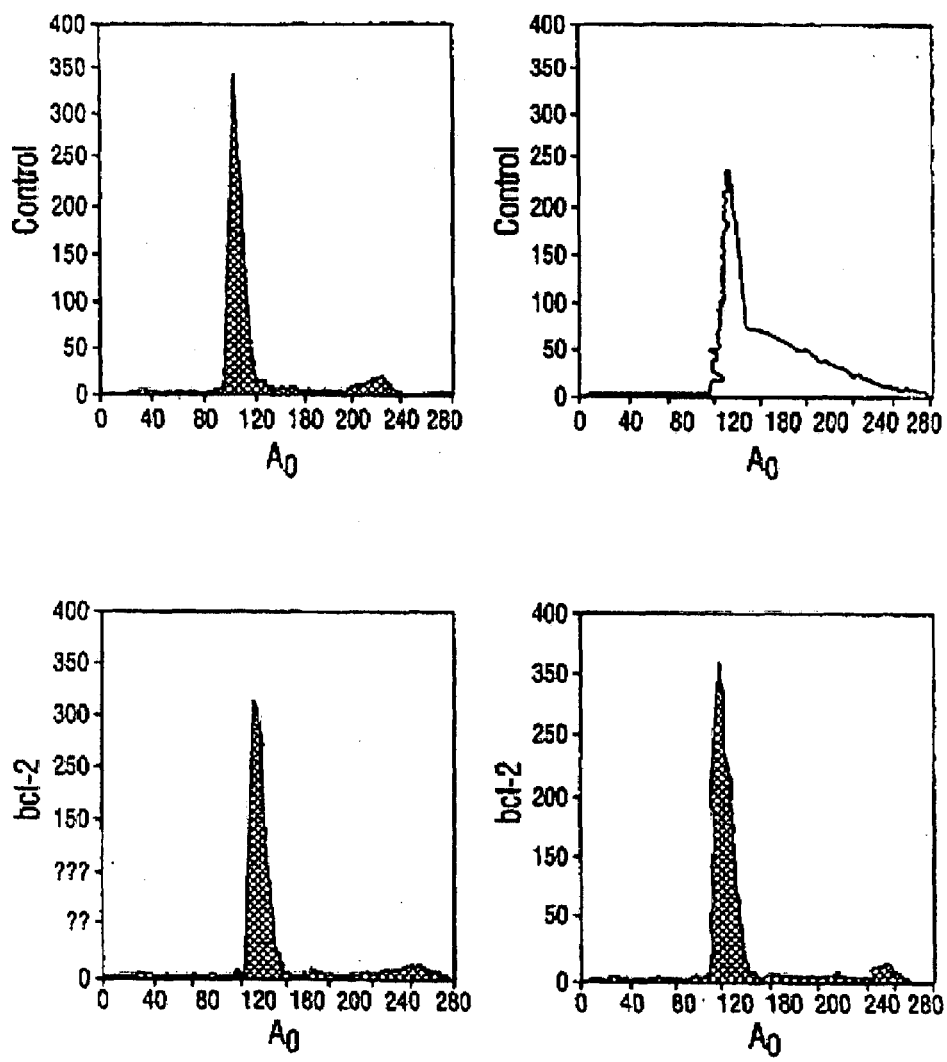

The human prostate carcinoma cell line, LNCaP, which possesses a wild-type p53 gene (Carroll et. al., *Prostate,* 23, 123-134, 1993), was selected to investigate the inhibition of p53-dependent programmed cell death by bcl-2. Stable bcl-2 expressing LNCaP prostate carcinoma cell lines were generated and confirmed by Western blotting. Expression of bcl-2 conferred significant resistance to apoptosis induction following γ-irradiation compared to control clones as assessed by morphologic and flow cytometric analysis (FIGS. 9A and 9B). No significant cell death induction was observed in bcl-2 expressing LNCaP cells up to 48 hours following irradiation. Additionally, there was no difference in cell cycle distribution between LNCaP and LNCaP-bcl-2 cells prior to irradiation and no evidence that the distribution of cells within the cell cycle was altered following irradiation. Approximately 60% of unirradiated control cells reside in $G_0/G_1$, 18% in S phase, and 22% in $G_2/M$ compared to 59% of unirradiated LNCaP-bcl-2 cells in $G_0/G_1$, 21% in S phase, and 20% in $G_2/M$. These values were not significantly different from those observed at 30 minutes, 1 hour, 2 hours, 4 hours, and 8 hours following irradiation.

Figure 10A:
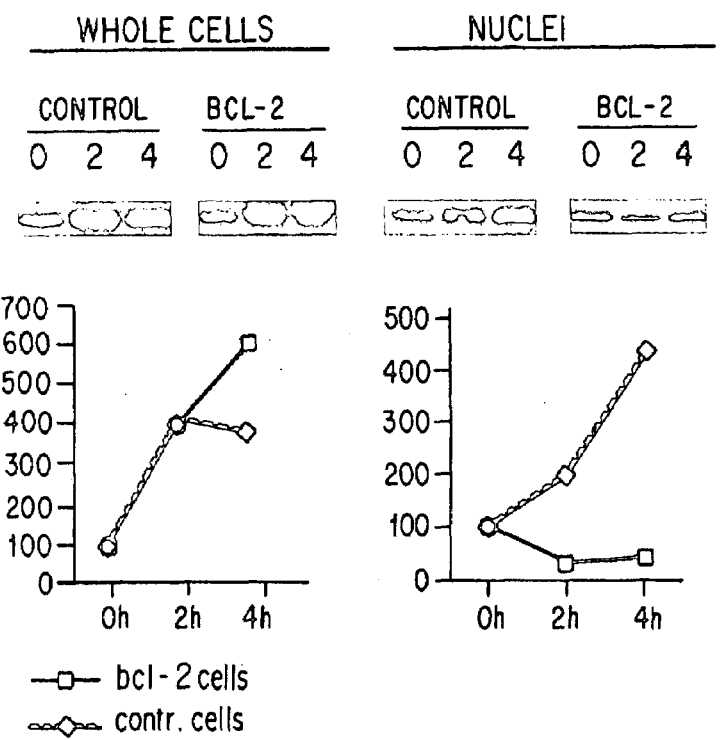
FIG. 10A & FIG. 10B & FIG. 10C: p53 induction, subcellular localization and transcriptional control.

Apoptosis induced in response to genotoxic damage is considered to be p53-dependent. In LNCaP cells, total cellular p53 protein was induced to approximately equivalent levels in bcl-2 expressing clones and control transfectants within 4 hours following 20 Gy γ-irradiation (FIG. 10A). Western blot analysis using isolated nuclei revealed that levels of p53 protein in the nucleus increased within 2 hours of irradiation in control LNCaP, but not in bcl-2 expressing LNCaP, cells (FIG. 10A). This observation suggests that the nuclear import of p53 following DNA damage may be impaired in the context of high levels of bcl-2 protein.

Figure 10B:
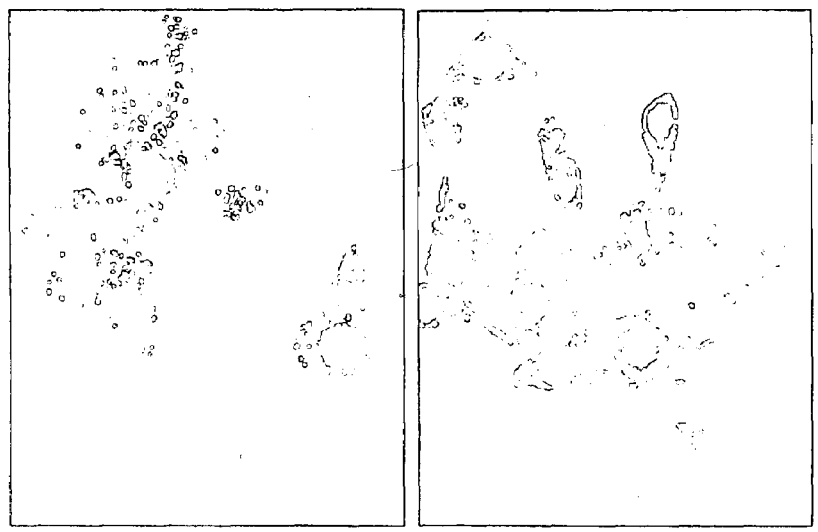

Scanning confocal laser microscopy was used to further characterize p53 nuclear import following irradiation. The inhibition of nuclear p53 import in the bcl-2 cells was confirmed by confocal microscopy using antibodies which recognize the p53 protein (FIG. 10B). Thus, by two independent techniques p53 nuclear import was demonstrated to be significantly inhibited in bcl-2 expressing cells following cell death induction by ionizing radiation.

Figure 10C:
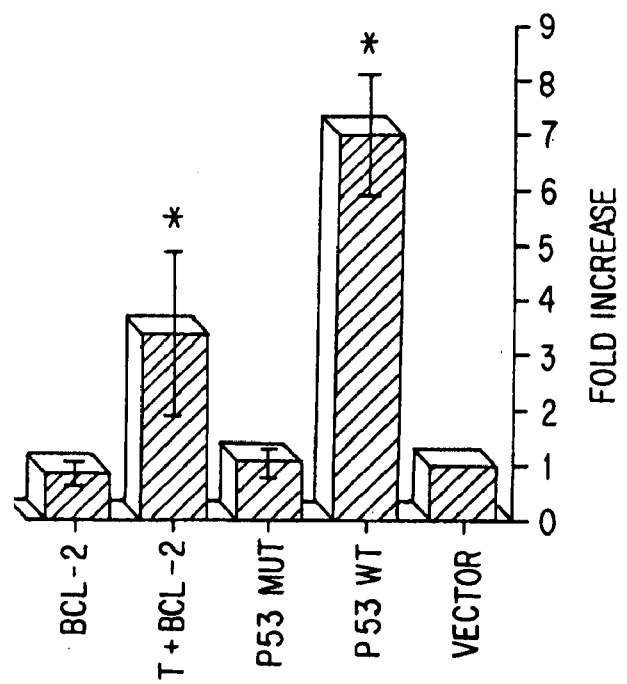
Figure 10C:
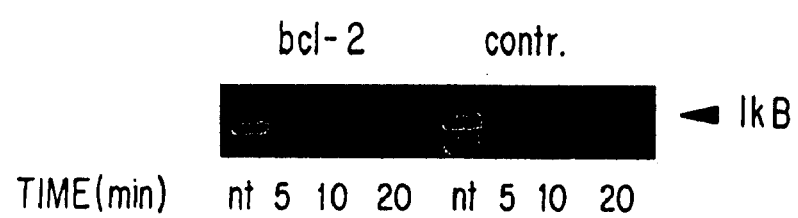

In order to determine whether the transactivating ability of p53 was affected in the context of bcl-2 protein. NIH3T3 cells were transiently transfected with an mdm-2 promoter-luciferase reporter construct which possesses functional p53 binding sites. Luciferase activity increased approximately 8-fold following co-transfection with a wild-type, but not mutant, p53 expression plasmid (FIG. 10C). Co-transfection of bcl-2 and wild-type p53 expression plasmids resulted in a 2-4 fold decrease in luciferase activity compared to wild-type p53 alone ($p \leq 0.02$).

Figure 11A:
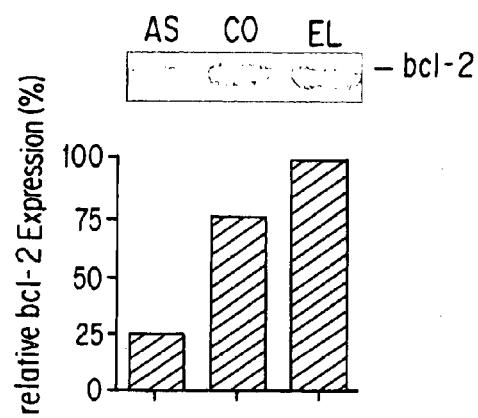
FIG. 11A & FIG. 11B: Downregulation of bcl-2 in RKO colon cancer cells by antisense oligonucleotides and localization of p53.
Figure 11B:
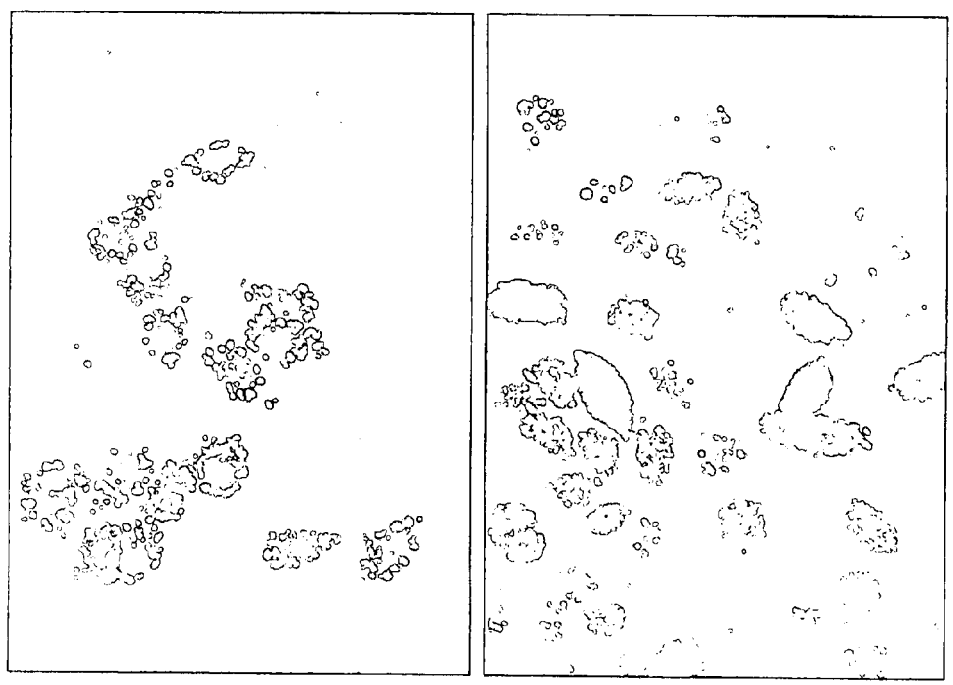

Additional studies were undertaken using the RKO colon carcinoma cell line to assess whether the ability of bcl-2 to inhibit the nuclear import of wild-type p53 was specific for the LNCaP prostate cancer cell line. RKO cells possess a wild-type p53 gene (Nagasawa et al. *CancerRes.*, 55, 1842-1846, 1995) and also express bcl-2 protein. To downregulate bcl-2 expression in RKO cells, bcl-2 specific antisense oligonucleotides were delivered by liposomes. Bcl-2 protein levels were reduced 3-fold compared to RKO cells treated with empty liposomes or liposomes containing control oligonucleotides (FIG. 11A). Confocal microscopy was used to image p53 protein 4 hours following 10 Gy of γ-radiation in RKO cells treated with liposomes containing antisense bcl-2 oligonucleotides, or control oligonucleotides. RKO cells treated with control oligonucleotides showed that most of the p53 protein remained localized in the cytosol (FIG. 11B). In contrast, RKO cells in which bcl-2 had been downregulated by antisense oligonucleotides exhibited high levels of p53 protein within the nucleus and significant ($p \leq 0.005$) cell death induction compared to RKO cells treated with control oligonucleotides (FIG. 11C). These findings suggest that the ability of bcl-2 to modulate the import of wild-type p53 protein in response to DNA damage is not cell-type specific.

Irradiation and Calcein-AM Staining

Cells were preloaded with calcein-AM (Molecular Probes, Eugene, Oreg.) at 1 mg/ml for 20 minutes in RPMI containing 10% FBS. Cells were given 20Gy of radiation using a $^{137}$Cs γ-source and calcein-generated fluorescence was visualized using epifluorescence optics and a FITC filter (530 nm emission). The 20Gy dose of radiation was selected as the minimum dose required to induce maximum levels of apoptosis in LNCaP cells.

Flow Cytometric Analysis

Flow cytometric analysis of cell cycle and cell death induction in LNCaP cells. Single cell suspensions were fixed in 70% ethanol and incubated with 50 mg/ml propidium iodide (PI) and 20 mg/ml RNAse for 15 min. at 37° C. Flow analysis was done with a EPICS Profile I at 488 nm excitation and collected for PI fluorescence using Elite Software 4.0 (Coulter Corp, Miami, Fla.) and the Multi Cycle DNA Analysis program software (Phoenix Flow Systems, San Diego, Calif.).

Transfections and Luciferase Assays

LNCaP cells were transfected with the splenic focus forming virus expression plasmid with, or without (control), the bcl-2 cDNA insert as previously described (Marin, et al. *Oncogene*, 12, 2259-66, 1996; Tu et al. *Cancer Lett.* 93, 147-155, 1995). The effector plasmids LTRXA and LTRKH expression plasmids have been described previously (Defile et al, 1993) and represent wild-type and mutant p53, respectively. The reporter plasmid P2mdm2-Luc was made by cloning a 1 Kb XhoI-fragment containing the p53 responsive element from the mouse mdm2 gene into the SmaI site of the pA3-luciferase plasmid. NIH3T3 cells were plated at a density of $0.5 \times 10^6$ cells per plate 24 hours before transfection. The effector wild type or mutant p53 plasmid (10 μg), reporter plasmid P2mdm2-Luc (4 μg) and β-galactosidase (βgal) expression plasmid (3 μg) were cotransfected with or without bcl-2 vector (20 μg) following the calcium-phosphate method. The total amount of DNA transfected was normalized adding p-GEM plasmid up to 37 μg of total DNA for all the transfections. At 48 hours after the transfection the cells were harvested. Extracts were made and assayed for luciferase activity.

Immunofluorescence Staining and Confocal Microscopy

LNCaPcontrol and LNCaP-bcl-2 cells were grown on laminin coated cover slides and irradiated with 20 Gy. After 4h, cells were washed twice with PBS, then fixed in 4% paraformaldehyde for ten minutes and washed twice in PBS. Cells were blocked with 10% goat serum in PBS, incubated with p53 (AB-2, Calbiochem) antibody in 10% goat serum (1:75), washed twice, and incubated with fluorescein isothiocyanate (FITC)-labeled secondary antibody in 10% goat serum (1:200). Imaging was done using a Zeiss scanning confocal laser microscope.

RKO cells were grown on laminin coated cover slides and incubated with liposomal oligonucleotide formulations at a final concentration of 10 μM at 37° C. in a 5% $CO_2$ incubator for 3 days. 4h after irradiation with 10 Gy, cells were washed twice with PBS, then fixed in 4% paraformaldehyde for ten minutes and washed twice in PBS. Cells were blocked with 10% goat serum in PBS, incubated with p53 (AB-2, Calbiochem) antibody in 10% goat serum (1:75), washed twice and incubated with fluorescein isothiocyanate (FITC)-labeled secondary antibody in 10% goat serum (1:200). Confocal microscopy was done using a Zeiss scanning laser confocal microscope.

Antisense & DNA Methods

P-ethoxy-oligonucleotides, a non-ionic and nuclease-resistant phosphodiester analog, were purchased from Oligo Therapeutics (Willsonville, Oreg.). An oligonucleotide specific for the translation initiation site of human bcl-2 mRNA: 5'CAGCGTGCGCCATCCTTC3' (SEQ ID NO:1) was used as antisense oligonucleotide. The control oligonucleotide used was a scrambled version of Bcl-2 antisense oligonucleotide 5'ACGGTCCGCCACTCCTTCCC3' (SEQ ID NO:2). P-ethoxy-oligonucleotides, dissolved in DMSO, were added to phospholipids (Avanti Polar Lipids, Alabaster, Ala.) in the presence of excess tert-butanol. The mixture was frozen in a dry ice/acetone bath, lyophilized overnight and hydrated with 0.9% saline at a final oligonucleotide concentration of 0.1 mmol/L. Empty liposomes were prepared identically as above, except that oligonucleotides were not included in the preparation. 0.25×105 cells/mL were seeded in a 24-well plate in 0.5 mL of the respective medium. Cells were incubated with antisense, control oligonucleotides and empty liposomes at final concentration of 10 µM at 37° C. in a 5% CO2 incubator for 3 days. Western blotting of whole cell extracts (40 µg) of control and bcl-2 transfected clones were analyzed by immunoblotting for bcl-2 protein using an anti-bcl-2 monoclonal antibody (Santa Cruz Biotechnology Inc, Santa Cruz, Calif.).

Analysis of Protein Expression in Cell and Nuclear Extracts

Western blot analysis of p53 protein induction and nuclear import following y-irradiation. Subconfluent cultures of control LNCaP and LNCaP-bcl-2 cells were irradiated with 20Gy. Extracts of nuclei were prepared by scraping cell monolayers into hypotonic lysis buffer (100 mM Hepes, pH 7.4, 1.5 mM $MgCl_2$, 10 mM KCl, 0.5 mM β-mercaptoethanol and 5 ng/ml leupeptin). After 10 minutes on ice, NP-40 was added to 0.625% and the crude nuclear pellet was recovered by centrifugation at 2000×g for 5 minutes. The nuclear pellets were lysed in SDS-PAGE sample loading buffer. Extracts of nuclei and whole cells were prepared 2 and 4 h after irradiation. Equivalent amounts of lysates were analyzed by immunoblotting with p53 antibody (Santa Cruz).

Extracts of nuclei were prepared by scraping cell monolayers into hypotonic lysis buffer (100 mM Hepes, pH 7.4, 1.5 mM $MgCl_2$, 10 mM KCl, 0.5 mM β-mercaptoethanol and 5 ng/ml leupeptin). After 10 minutes on ice, NP-40 was added to 0.625% and the crude nuclear pellet was recovered by centrifugation at 2000×g for 5 minutes. The nuclear pellets were lysed in SDS-PAGE sample loading buffer.

Example 5

In vivo Testing

In an initial round of in vivo trials, 30 nude (nu/nu) mice, aged about 5-6 weeks were each injected intraperitoneally with 3 million Johnson cells, follicular lymphoma cells bearing the t(14;18) translocation. Three groups of 10 mice each were used: untreated mice (group I), liposomal p-ethoxy Bcl-2 antisense treated mice (group II) and liposoml Bcl-2 control treated mice (group III). One week after tumor implantation, groups II and III mice were administered a biweekly intravenous injection of liposomal Bcl-2 antisense oligos, or liposomal Bcl-2 control oligos. The oligo dose is 15 mg/kg of mouse body weight.

Some mice were observed to reach the moribund state (which is defined as tumor size exceeding 1.5 $cm^3$) by day 50. On day 70 after implantation (63 days of treatement) six mice (60%) in groups I and III had reached moribund state and were sacrificed, while only 2 mice (20%) in group II had reached moribund state and were sacrificed. One other mouse reached moribund state by day 77 (70 days of treatment). The study was terminated on day 78. Tissue from liver, kidney, spleen, heart, lungs, stomach, intestines and bone marrow were collected for histopathology studies. Thus preliminary in vivo results indicate that the antisense Bcl-2 delivered in neutral liposomes are effective in inhibiting follicular lymphoma in mice.

Example 6

Clinical Trials

This example is concerned with the development of human treatment protocols using the lipid-associated oligo- and polynucleotide compositions. These lipid formulations will be of use in the clinical treatment of various bcl-2-overexpressing cancers and diseases in which transformed or cancerous cells play a role. Such treatment will be particularly useful tools in anti-tumor therapy, for example, in treating patients with FL. This treatment will also be useful in treating other conditions that are mediated by bcl-2 over-expression and resistant to conventional regimens and treatments such as hematologic malignancies, both leukemias and lymphomas, including follicular and nonfollicular lymphomas, chronic lymphocytic leukemia, and plasma cell dyscrasias; solid tumors like those associated with breast, prostate and colon cancer; and immune disorders.

The various elements of conducting a clinical trial, including patient treatment and monitoring, will be known to those of skill in the art in light of the present disclosure. The following information is being presented as a general guideline for use in establishing lipid-associated oligo-and polynucleotide compositions alone or in combinations with anti-cancer drugs in clinical trials.

Candidates for the phase I clinical trial will be patients on which all conventional therapies have failed. Liposomal Bcl-2 antisense oligos will be administered to them intravenously on a tentative weekly basis. To monitor disease course and evaluate the anti-tumor responses, it is contemplated that the patients should be examined for appropriate tumor markers every month. To assess the effectiveness of the drug, the following parameters will be monitored: tumor size and bone marrow infiltration of the cancer cells. Tests that will be used to monitor the progress of the patients and the effectiveness of the treatments include: physical exam, X-ray, blood work and other clinical laboratory methodologies. In addition, peripheral blood and bone marrow samples will be drawn to assess the modification of the target protein expression. The doses given in the phase I study will be escalated as is done in standard phase I clinical phase trials, i.e. doses will be escalated until maximal tolerable ranges are reached.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

Example 7

Human Treatment and Clinical Protocols

This example describes a protocol to facilitate the treatment of bcl-2-mediated diseases using lipid-associated oligo- or polynucleotide compositions alone or in combination with anti-cancer drugs.

Typically, patients that are candidates for treatment are those with FL although patients with hematologic malignancies, both leukemias and lymphomas; solid tumors like those associated with breast, prostate and colon cancer; and immune disorders may also be treated with the methods of this invention. The typical course of treatment will vary depending upon the individual patient and disease being treated in ways known to those of skill in the art. For example, a patient with FL might be treated in eight week cycles, although longer duration may be used if no adverse effects are observed with the patient, and shorter terms of treatment may result if the patient does not tolerate the treatment as hoped. Each cycle will consist of between 20 and 35 individual doses spaced equally, although this too may be varied depending on the clinical situation.

A patient presenting a bcl-2-mediated condition, like FL, may be treated using the following protocol. Patients may, but need not, have received previous chemo-, radio- or gene therapeutic treatments. Optimally the patient will exhibit adequate bone marrow function (defined as peripheral absolute granulocyte count of >2,000/mm$^3$ and platelet count of 100, 000 μmm$^3$, adequate liver function (bilirubin 1.5 mg/dl) and adequate renal function (creatinine 1.5 mg/dl).

The over-expression of bcl-2 is typically monitored before, during, and after the therapy. A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The lipid-associated oligo- or poly-nucleotide compositions may be delivered to the patient before, after or concurrently with the other anti-cancer agents.

A typical treatment course may comprise about six doses delivered over a 7 to 21 day period. Upon election by the clinician the regimen may be continued with six doses every three weeks or on a less frequent (monthly, bimonthly, quarterly etc.) basis. Of course, these are only exemplary times for treatment, and the skilled practitioner will readily recognize that many other time-courses are possible.

To kill bcl-2-overexpressing cancer cells using the methods and compositions described in the present invention one will generally contact a target cell with the lipid-associated formulations described previously. These compositions will be provided in an amount effective to kill or inhibit the proliferation of the cell.

Regional delivery of the lipid-associated formulations will be an efficient method for delivering a therapeutically effective dose to counteract the clinical disease. Alternatively systemic delivery may be appropriate. The therapeutic composition of the present invention may be administered to the patient directly at the site of the tumor. This is in essence a topical treatment of the surface of the cancer. The volume of the composition should usually be sufficient to ensure that the entire surface of the tumor is contacted by the lipid-associated oligo- or poly-nucleotide composition.

In one embodiment, administration simply entails injection of the therapeutic composition into the tumor. In another embodiment, a catheter is inserted into the site of the tumor and the cavity may be continuously perfused for a desired period of time.

Of course, the above-described treatment regimes may be altered in accordance with the knowledge gained from clinical trials such as those described in Example 5. Those of skill in the art will be able to take the information disclosed in this specification and optimize treatment regimes based on the clinical trials described in the specification.

---

The invention claimed is:

1. A composition comprising a P-ethoxy polynucleotide that hybridizes to a Bcl-2-encoding polynucleotide under intracellular conditions and a neutral lipid associated with said P-ethoxy polynucleotide to form a neutrally-charged polynucleotide/lipid association.

2. The composition of claim 1, wherein said P-ethoxy polynucleotide is an oligonucleotide having a length of between about 8 and about 50 bases.

3. The composition of claim 1, wherein the P-ethoxy polynucleotide is complementary to the translation initiation site of Bcl-2 mRNA.

4. The composition of claim 3, wherein the polynucleotide is an oligonucleotide comprising the sequence CAGCGTGCGCCATCCTTC (SEQ ID NO:1).

5. The composition of claim 1, comprising a liposome formed from the neutral lipid.

6. The composition of claim 5, wherein the P-ethoxy polynucleotide is encapsulated in the liposome.

7. The composition of claim 1, wherein the neutral lipid is a phosphatidylcholine, a phosphatidylglycerol, or a phosphatidylethanolamine.

8. The composition of claim 7, wherein the neutral lipid is dioleoylphosphatidylcholine.

9. A composition comprising an expression construct that encodes a P-ethoxy polynucleotide that hybridizes to a Bcl-2-encoding polynucleotide under intracellular conditions, wherein said P-ethoxy polynucleotide is under the control of a promoter that is capable of expressing in eukaryotic cells, and wherein said construct is associated with a neutral lipid to form a neutrally-charged polynucleotide/lipid association.

10. A method of inhibiting a Bcl-2-associated cancer comprising obtaining an antisense polynucleotide that hybridizes to a Bcl-2-encoding polynucleotide under intracellular conditions, mixing the antisense polynucleotide with a neutral lipid to form a polynucleotide/lipid association, and administering said association to a Bcl-2 associated cancer cell, thereby inhibiting growth of said cancer cell.

11. The method of claim 10, wherein said cancer cell is a follicular lymphoma cell.

12. The method of claim 10, wherein said polynucleotide is an oligonucleotide having a length of between about 8 and about 50 bases.

13. The method of claim 10, comprising a liposome formed from the neutral lipid.

14. The method of claim 13, wherein the liposome encapsulates the P-ethoxy polynucleotide.

15. The method of claim 10, wherein said administering takes place in an animal.

16. The method of claim 15, wherein said animal is a human.

17. The method of claim 16, wherein said association is delivered to said human in a volume of 0.50-10.0 ml per dose.

18. The method of claim 16, wherein said association is delivered to said human in an amount of from about 5 to about 30 mg polynucleotide per $m^2$.

19. The method of claim 18, wherein said association is administered three times per week for eight weeks.

20. The composition of claim 5, wherein said liposome consists essentially of neutral lipids.

21. The composition of claim 9, comprising a liposome formed from said neutral lipid.

22. The composition of claim 21, wherein said liposome consists essentially of neutral lipids.

23. The method of claim 10, wherein said antisense polynucleotide is a P-ethoxy polynucleotide.

24. A neutral lipid oligonucleotide association comprising a neutral lipid associated with an antisense oligonucleotide of from about 8 to about 50 bases and complementary to the translation initiation site of Bcl-2 mRNA, wherein said translation initiation site comprises the sequence CAGCGTGCGCCATCCTTC (SEQ ID NO:1).

25. The neutral lipid oligonucleotide association of claim 24, wherein the oligonucleotide has the sequence CAGCGTGCGCCATCCTTC (SEQ ID NO:1).

26. The neutral lipid oligonucleotide association of claim 24, comprising a liposome formed from the lipid.

27. The neutral lipid oligonucleotide association of claim 26, wherein the oligonucleotide is encapsulated in the liposome.

28. The neutral lipid oligonucleotide association of claim 26, wherein said liposome consists essentially of neutral lipids.

29. The neutral lipid oligonucleotide association of claim 24, wherein the lipid is a phosphatidylcholine, a phosphatidylglycerol, or a phosphatidylethanolamine.

30. The neutral lipid oligonucleotide association of claim 29, wherein the lipid is dioleoylphosphatidylcholine.

31. A composition comprising a neutral lipid associated with an expression construct that encodes an oligonucleotide of from about 8 to about 50 bases and complementary to at least 8 bases of the translation initiation site of Bcl-2 mRNA, wherein the construct is under the control of a promoter that is capable of expressing peptides in eukaryotic cells.

32. The composition of claim 31, comprising a liposome formed from the lipid.

33. The composition of claim 32, wherein said liposome consists essentially of neutral lipids.

34. A composition comprising a first antisense polynucleotide that hybridizes to a second, Bcl-2-encoding polynucleotide under intracellular conditions and a primary phosphatide associated with said first polynucleotide, wherein said primary phosphatide is a neutral lipid, and wherein said first polynucleotide comprises at least 8 nucleotides of the sequence CAGCGTGCGCCATCCTTC (SEQ ID NO:1), and wherein said polynucleotide is complementary to the translation initiation site of Bcl-2.

35. The composition of claim 34, comprising a liposome formed from the primary phosphatide.

36. The composition of claim 35, wherein said liposome consists essentially of neutral lipids.

37. A method of inhibiting a Bcl-2-associated cancer comprising:
   a) obtaining an antisense polynucleotide that hybridizes to a Bcl-2-encoding polynucleotide under intracellular conditions;
   b) mixing the antisense polynucleotide with a neutral lipid to form a polynucleotide/lipid association; and
   c) administering said association to a cell,
wherein said cell expresses both Bcl-2 and Bax, the growth of said cell is inhibited, and the non-specific toxicity of said association is less than the non-specific toxicity of the antisense polynucleotide with DMPC.

38. The method of claim 37, wherein said cancer cell is a follicular lymphoma cell.

39. The method of claim 37, wherein said polynucleotide is an oligonucleotide having a length of between about 8 and about 50 bases.

40. The method of claim 37, comprising a liposome formed from said neutral lipid.

41. The method of claim 40, wherein the liposome encapsulates said antisense polynucleotide.

42. The method of claim 37, wherein said administering takes place in an animal.

43. The method of claim 42, wherein said animal is a human.

44. The method of claim 43, wherein said association is delivered to said human in a volume o(Previously presented)f 0.50-10.0 ml per dose.

45. The method of claim 43, wherein said association is delivered to said human in an amount of from about 5 to about 30 mg polynucleotide per $m^2$.

46. The method of claim 45, wherein said association is administered three times per week for eight weeks.

* * * * *